US006416510B1

(12) United States Patent
Altman et al.

(10) Patent No.: US 6,416,510 B1
(45) Date of Patent: Jul. 9, 2002

(54) DRUG DELIVERY CATHETERS THAT ATTACH TO TISSUE AND METHODS FOR THEIR USE

(75) Inventors: Peter A. Altman; John D. Altman; Simon Stertzer, all of South San Francisco, CA (US)

(73) Assignee: Biocardia, Inc., South San Francisco, CA (US)

(*) Notice: Subject to any disclaimer, the term of this patent is extended or adjusted under 35 U.S.C. 154(b) by 0 days.

(21) Appl. No.: 09/418,205

(22) Filed: Oct. 13, 1999

Related U.S. Application Data

(63) Continuation-in-part of application No. 08/816,850, filed on Mar. 13, 1997.

(51) Int. Cl.[7] .................................................. A61N 1/05
(52) U.S. Cl. .......................... 606/41; 607/120; 607/3
(58) Field of Search .............................. 607/120, 121, 607/122, 123, 3, 126, 127, 128, 60–61, 32–33; 606/41, 45, 47, 48, 44, 167; 600/508, 374; 604/22, 264, 95, 200, 73, 181, 187, 131, 141, 143, 148, 280

(56) References Cited

U.S. PATENT DOCUMENTS

| | | | |
|---|---|---|---|
| 4,296,100 A | 10/1981 | Franco | 424/108 |
| 4,892,538 A | 1/1990 | Aebishcher et al. | 604/891.1 |
| 5,002,067 A | 3/1991 | Berthelson | 128/786 |
| 5,244,460 A | 9/1993 | Unger et al. | 604/53 |
| 5,283,187 A | 2/1994 | Aebischer et al. | 435/182 |
| 5,322,064 A | 6/1994 | Lundquist | 128/4 |
| 5,324,325 A | 6/1994 | Moaddeb | 607/120 |
| 5,385,148 A | 1/1995 | Lesh et al. | 128/662.06 |
| 5,405,376 A | 4/1995 | Lindquist | 128/642 |
| 5,431,649 A | 7/1995 | Mulier | 606/41 |
| 5,447,533 A | 9/1995 | Vachon | 607/120 |
| 5,527,344 A | 6/1996 | Arzbaecher | 607/3 |
| 5,531,780 A | 7/1996 | Vachon | 607/120 |
| 5,551,427 A | 9/1996 | Altman | 128/642 |
| 5,661,133 A | 8/1997 | Leiden et al. | 514/44 |
| 5,693,622 A | 12/1997 | Wolff et al. | 514/44 |
| 5,698,531 A | 12/1997 | Nabel et al. | 514/44 |
| 5,702,384 A | * 12/1997 | Umeyama et al. | 604/892.1 |
| 5,704,910 A | 1/1998 | Humes | 604/52 |
| 5,807,395 A | 9/1998 | Mulier et al. | 606/41 |
| 5,840,059 A | * 11/1998 | March et al. | 604/53 |
| 6,086,582 A | 6/2000 | Altman | 606/41 |
| 6,102,887 A | 8/2000 | Altman | 604/22 |
| 6,165,188 A | * 12/2000 | Saadat et al. | 606/159 |
| 6,238,406 B1 | * 5/2001 | Ellis et al. | 606/167 |

OTHER PUBLICATIONS

Scheinman, Supraventricular Tachyarrhythmias: Drug Therapy Versus Catheter Ablation, 17 Clinical Cardiology II–ll (1994).

(List continued on next page.)

*Primary Examiner*—Marvin M. Lateef
*Assistant Examiner*—Eleni Mantis Mercader
(74) *Attorney, Agent, or Firm*—K. David Crockett, Esq.; Crockett & Crockett

(57) ABSTRACT

A drug delivery catheter suited for cardiac procedures. The catheter includes a distal helical coil or other fixation and penetrating element which can be operated from the proximal end of the catheter to engage and penetrate the myocardium. Once delivered to the inside of the heart, the catheter can be used to inject small doses of therapeutic agents to the myocardium. The drug delivery system of the catheter allows for precise control of the dose injected into the heart wall.

24 Claims, 15 Drawing Sheets

OTHER PUBLICATIONS

Lazarous et al., Comparative Effects of Basic Fibroblast Growth Factor and Vascular Response to Injury, 94 Circulation 1074–1082 (Sep. 1996).

Lin et al., Expression of Recombinant Genes In Myocardium In Vivo After Direct Injection of DNA, 82 Circulation 2217–2221 (Dec. 1990).

French et al., Direct In Vivo Gene Transfer into Porcine myocardium using Replication Deficient Adenoviral Vectors, 90 Circulation 2414–2424 (Nov. 1994).

Mulhauser et al., Safety and Efficacy of In Vivo Gene Transfer into the Porcine Heart with Replication–deficient, Recombinant Adenovirus Vectors, 3 Gene Therapy 145–153 (1996).

Arras et al., The Delivery of Angiogenic Factors to the Heart be Microsphere Therapy, 16 Nature Biotechnology (Feb. 1998).

* cited by examiner

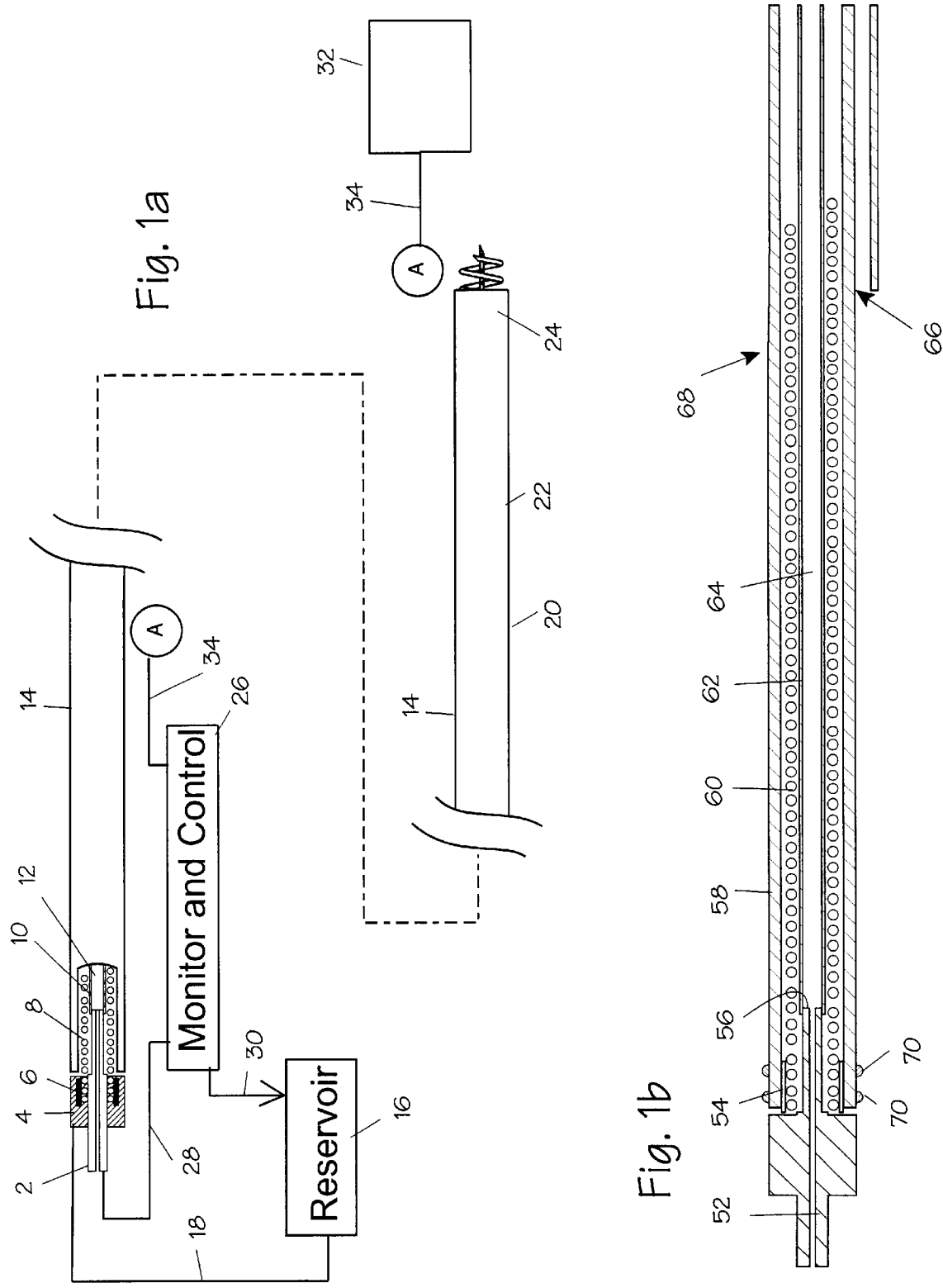

8A

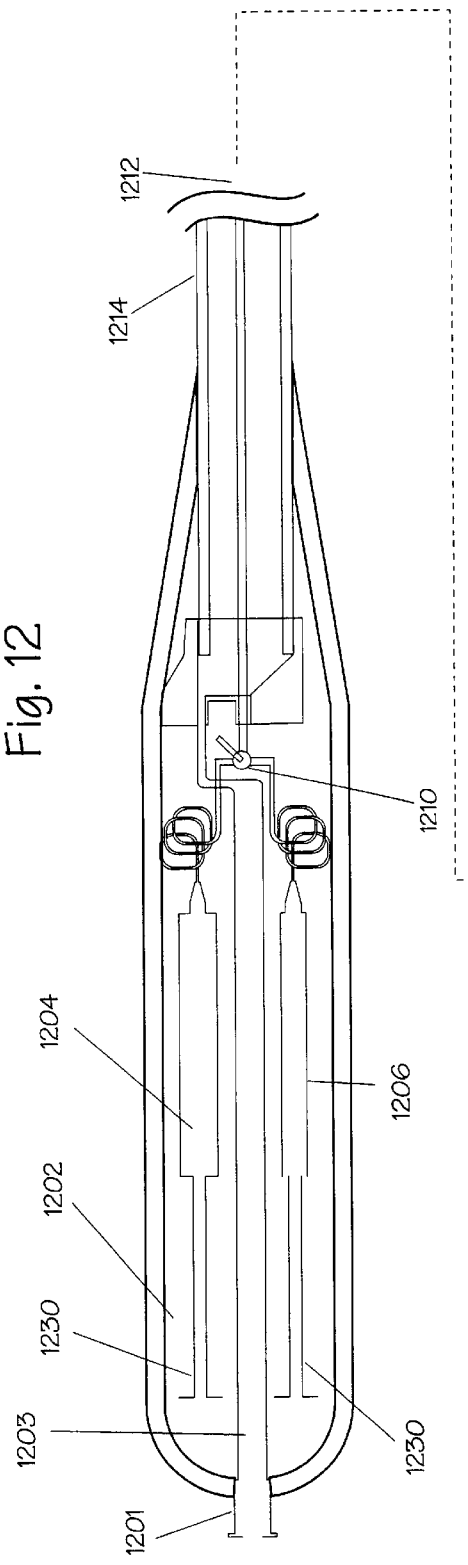
Fig. 12
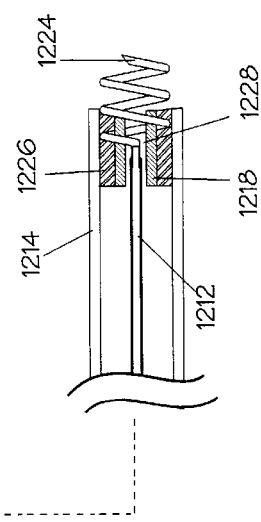
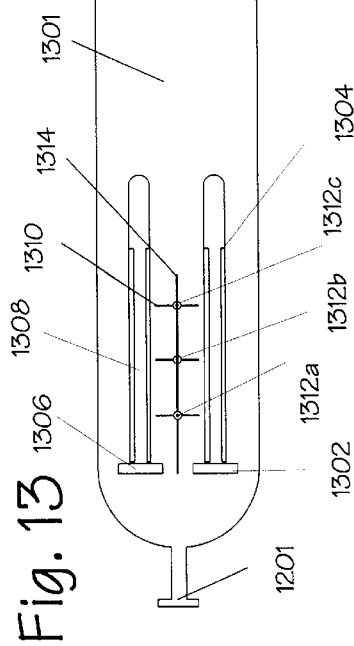
Fig. 13

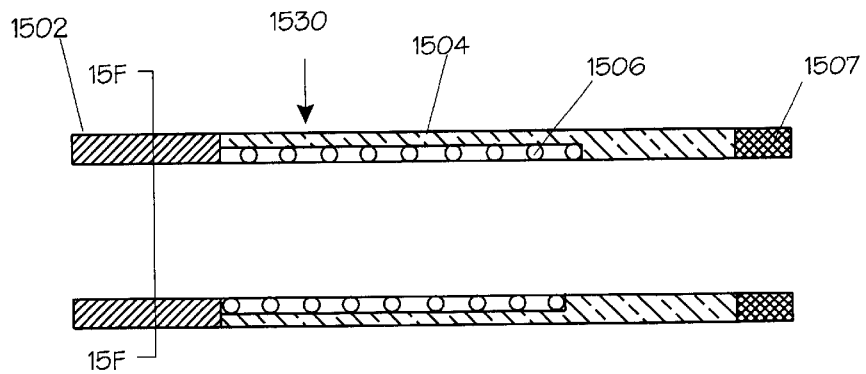
Fig. 15A
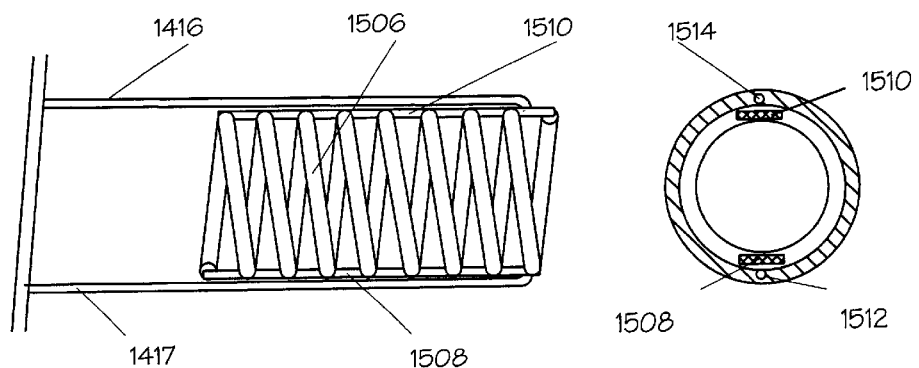
Fig 15B
Fig. 15C
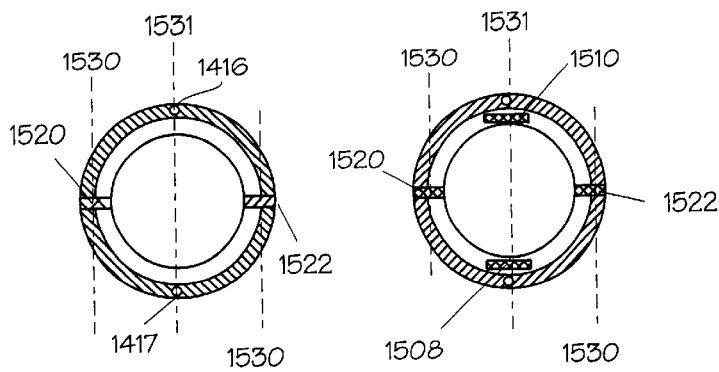
Fig 15D
Fig. 15E
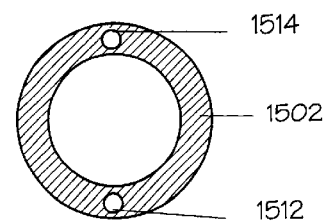
Fig. 15F

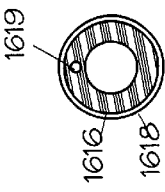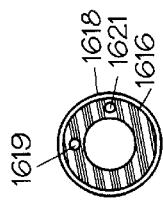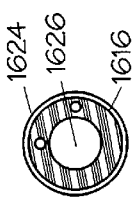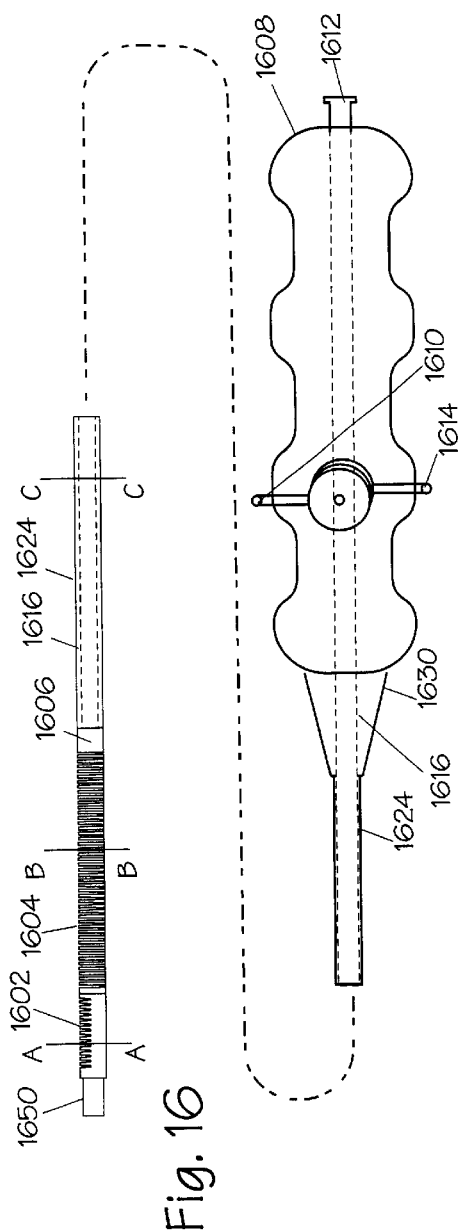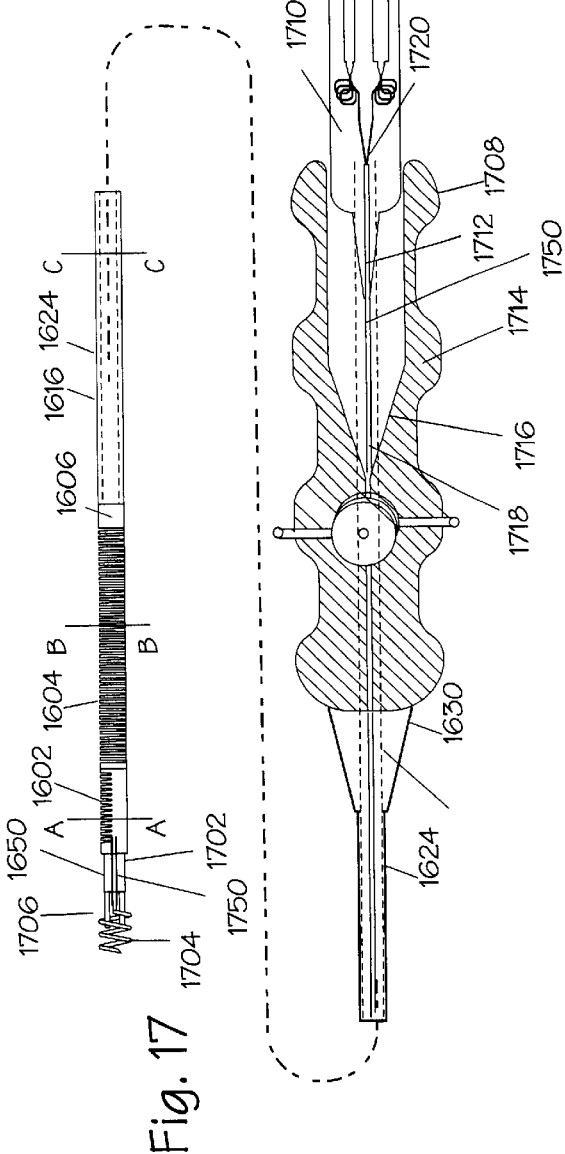

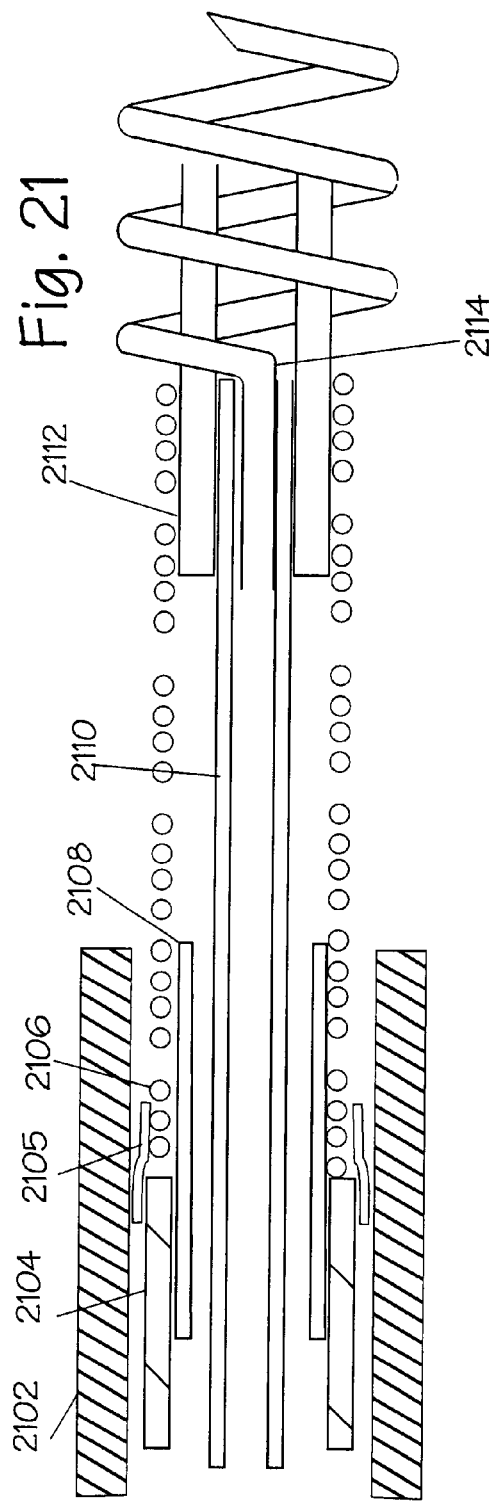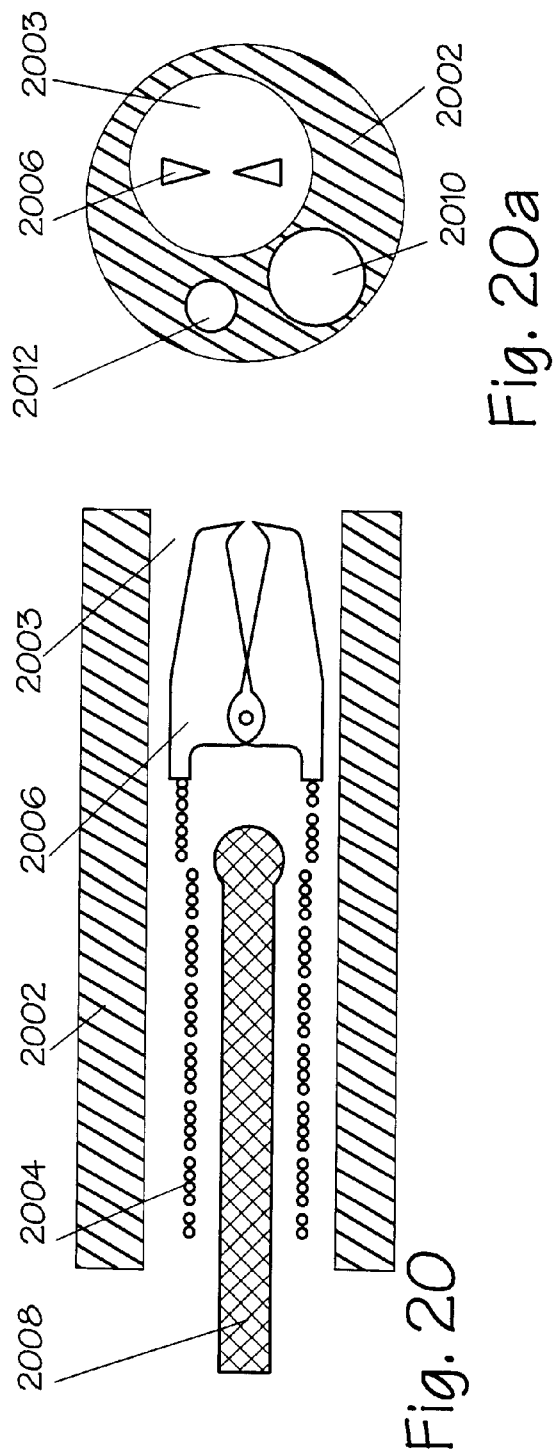

DRUG DELIVERY CATHETERS THAT ATTACH TO TISSUE AND METHODS FOR THEIR USE

This application is a continuation-in-part of co-pending U.S. application Ser. No. 08/816,850 filed Mar. 13, 1997.

FIELD OF THE INVENTIONS

The inventions described below relate to site specific delivery of therapeutic agents, structures and catheter systems to achieve site specific delivery of therapeutic agents, and means for implanting and using these systems to enable delivery of therapeutic agents to the body.

These systems also have importance for new procedures that have been called percutaneous transmyocardial revascularization or PTMR.

BACKGROUND OF THE INVENTION

It is possible to identify particular sites within the myocardium which may benefit from local drug release therapy. Examples of problematic tissue which may benefit from local drug release therapy are ischemic sites and arrhythmogenic sites. Different means and methods for delivering agents to these sites will be disclosed in detail. These specific discussions should in no way limit the scope of the devices disclosed for treating other tissues with other agents.

Ischemic Sites

Ischemic tissue is characterized by limited metabolic processes which causes poor functionality. The metabolism is limited because the tissue lacks oxygen, nutrients, and means for disposing of wastes. In turn this hinders the normal functioning of the heart cells or myocytes in an ischemic region. If an ischemic, or damaged, region of the heart does not receive enough nutrients to sustain the myocytes they are said to die, and the tissue is said to become infarcted. Ischemia is reversible, such that cells may return to normal function once they receive the proper nutrients. Infarction is irreversible.

A number of methods have been developed to treat ischemic regions in the heart. Noninvasive systemic delivery of anti-ischemic agents such as nitrates or vasodilators allows the heart to work less by reducing vascular resistance. Some vascular obstructions are treated by the systemic delivery of pharmacological agents such as TPA, urokinase, or antithrombolytics which can break up the obstruction. Catheter based techniques to remove the vascular obstructions such as percutaneous transluminal coronary angioplasty (PTCA), atherectomy devices, and stents can increase myocardial perfusion. More drastic, but very reliable procedures such as coronary artery bypass surgery can also be performed. All of these techniques treat the root cause of poor perfusion.

It should be noted that these therapies are primarily for the treatment of large vessel disease, and that many patients suffer from poor perfusion within many of the smaller vessels. These smaller vessels cannot be treated with conventional therapies.

The delivery of angiogenic growth factors to the heart via the coronary arteries by catheter techniques, or by implantable controlled release matrices, can create new capillary vascular growth within the myocardium. Recent work has shown substantial increases in muscular flow in a variety of in vivo experimental models with growth factors such as basic fibroblast growth factor (bFGF), vascular endothelial growth factor (VEGF), and acidic fibroblast growth factor (aFGF). The methods of delivering these agents to the heart have included implantable controlled release matrices such as ethylene vinyl acetate copolymer (EVAC), and sequential bolus delivery into the coronary arteries. Recently similar techniques have been attempted in peripheral vessels in human patients with the primary difficulty being systemic effects of the agents delivered. "Angiogenic agents" and "endothelial agents" are active agents that promote angiogenesis and/or endothelial cell growth, or if applicable, vasculogenesis. This would include factors such as those discussed that accelerate wound healing such as growth hormone, insulin like growth factor-I (IGF-I), VEGF, VIGF, PDGF, epidermal growth factor (EGF), CTGF and members of its family, FGF, TGF-a and TGF B. The most widely recognized angiogenic agents include the following: VEGF-165, VEGF-121, VEGF-145, FGF-2, FGF-I, Transforming Growth Factor (TGF-B), Tumor Necrosis Factor a (TMF a), Tumor Necrosis Factor B (TMF B), Angiogenin, Interleukin-8, Proliferin, Prostaglandins (PGE), Placental Growth factor, Granulocyte Growth Factor, Platelet Derived Endothilail Cell Growth Factor, Hepatocyte Growth Factor, DEL-1, Angiostatin-1 and Pleiotrophin.

"Angiostatic agents" are active agents that inhibit angiogenesis or vasculogenesis or otherwise inhibit or prevent growth of cancer cells. Examples include antibodies or other antagonists to angiogenic agents as defined above, such as antibodies to VEGF or Angiotensin 2. They additionally include cytotherapeutic agents such as cytotoxic agents, chemotherapeutic agents, growth inhibitory agents, apoptotic agents, and other agents to treat cancer, such as anti-HER-2, anti CD20, and other bioactive and organic chemical agents.

Polypeptide agents may be introduced by expression in vivo, which is often referred to as gene therapy. There are two major approaches for getting the nucleic acid (optionally containing a vector) into the patients cells: in vivo and ex vivo. For in vivo delivery, the nucleic acid is injected directly into the patient, usually at the site where desired. For ex-vivo delivery, the patients cells are removed, the nucleic acid is introduced into these isolated cells, and the modified cells are administered to the patient either directly or via encapsulation within porous membranes that are implanted into the patient (see U.S. Pat. Nos. 4,892,538 and 5,283,187).

The preferred embodiment of this invention is the delivery of therapeutic molecules from micro drug delivery systems such as liposomes, nanoparticles, biodegradable controlled release polymer matrices, and biodegradable microspheres which are well known in the literature. These have been described briefly in U.S. application Ser. No. 08/816,850.

The agents to be delivered may include one or more small molecules, macromolecules, liposomal encapsulations of molecules, microdrug delivery system encapsulation of therapeutic molecules, covalent linking of carbohydrates and other molecules to a therapeutic molecules, and gene therapy preparations. These will be briefly defined.

"Small molecules" may be any smaller therapeutic molecule, known or unknown. Examples of known small molecules relative to cardiac delivery include the antiarrhythmic agents that affect cardiac excitation. Drugs that predominantly affect slow pathway conduction include digitalis, calcium channel blockers, and beta blockers. Drugs that predominantly prolong refractoriness, or time before a heart cell can be activated, produce conduction block in either the fast pathway or in accessory AV connections including the class IA antiarrhythmic agents (quinidine, procainimide, and disopyrimide) or class IC drugs (flecainide and propefenone). The class III antiarrhythmic agents (sotolol or amiodorone) prolong refractoriness and delay or block conduction over fast or slow pathways as well as in accessory AV connections. Temporary blockade of slow pathway conduction usually can be achieved by intravenous administration of adenosine or verapamil. [Scheinman, Melvin: Supraventricular Tachycardia: Drug Therapy Versus Catheter Ablation, Clinical Cardiology Vol 17, Suppl. II-11-II-15 (1994)]. Many other small molecule agents are possible, such as poisonous or toxic agents designed to damage tissue that have substantial benefits when used locally such as on a tumor. One example of such a small molecule to treat tumors is doxarubicin.

A "macromolecule" is any large molecule and includes proteins, nucleic acids, and carbohydrates. Examples of such macromolecules include the growth factors, Vascular Endothelial Growth Factor, basic Fibroblastic Growth Factor, and acidic Fibroblastic Growth Factor, although others are possible. Examples of macromolecular agents of interest for local delivery to tumors include angiostatin, endostatin, and other antiangiogenic agents.

A "Liposome" refers to an approximately spherically shaped bilayer structure comprised of a natural or synthetic phospholipid membrane or membranes, and sometimes other membrane components such as cholesterol and protein, which can act as a physical reservoir for drugs. These drugs may be sequestered in the liposome membrane or may be encapsulated in the aqueous interior of the vesicle. Liposomes are characterized according to size and number of membrane bilayers.

A "gene therapy preparation" is broadly defined as including genetic materials, endogenous cells previously modified to express certain proteins, exogenous cells capable of expressing certain proteins, or exogenous cells encapsulated in a semi-permeable micro device. This terminology is stretched beyond its traditional usage to include encapsulated cellular materials as many of the same issues of interstitial delivery of macrostructures apply.

The term "genetic material" generally refers to DNA which codes for a protein, but also encompasses RNA when used with an RNA virus or other vector based upon RNA. Transformation is the process by which cells have incorporated an exogenous gene by direct infection, transfection, or other means of uptake. The term "vector" is well understood and is synonymous with "cloning vehicle". A vector is nonchromosomal double stranded DNA comprising an intact replicon such that the vector is replicated when placed within a unicellular organism, for example by a process of transformation. Viral vectors include retroviruses, adenoviruses, herpesvirus, papovirus, or otherwise modified naturally occurring viruses. Vector also means a formulation of DNA with a chemical or substance which allows uptake by cells. In addition, materials could be delivered to inhibit the expression of a gene. Approaches include: antisense agents such as synthetic oligonucleotides which are complimentary to RNA or the use of plasmids expressing the reverse compliment of a gene, catalytic RNA's or ribozymes which can specifically degrade RNA sequences, by preparing mutant transcripts lacking a domain for activation, or over express recombinant proteins which antagonize the expression or function of other activities. Advances in biochemistry and molecular biology in recent years have led to the construction of recombinant vectors in which, for example, retroviruses and plasmids are made to contain exogenous RNA or DNA respectively. In particular instances the recombinant vector can include heterologous RNA or DNA by which is meant RNA or DNA which codes for a polypeptide not produced by the organism susceptible to transformation by the recombinant vector. The production of recombinant RNA and DNA vectors is well understood and need not be described in detail. Such gene therapy preparations could be delivered in a variety of fluid agents, one of which is phosphate buffered saline.

Details on microencapsulated cells are described in U.S. Pat. No. 5,698,531 and additional details on the delivery of genetic material are described in U.S. Pat. No. 5,704,910. Both of these patents describe the potential of delivering such agents endoluminally within a blood vessel. Neither of these provides a means to deliver such agents at a depth within the heart muscle, and neither of them recognizes the potential of this approach. U.S. Pat. No. 5,661,133 does recognize the potential for delivering genes to the heart, but does not describe the means of delivery other than by injection.

U.S. Pat. No. 5,244,460 issued to Unger describes a method of introducing growth factors over time by delivering them through fluid catheters into the coronary arteries, but this does not result in efficient delivery of these agents to the ischemic tissue. If these or other agents are delivered to the coronary, a region of tissue that is equivalent to that supplied by the artery will receive the therapeutic agents. This may be substantially more tissue than is in need of local drug delivery therapy. Further, if a vessel is occluded, the growth factors will act in the tissue which the coronary arteries successfully perfuse. As the underlying problem of ischemic tissue is poor perfusion, excess growth factor must be delivered in order to obtain the desired effects in the poorly perfused tissue. Further, growth factors may cause unwanted angiogenesis in tissues where inappropriately delivered. The cornea is described by Unger as such a location, but perhaps more critical is inappropriate delivery of these factors to the brain. Further, placement of delivery devices within these coronary arteries as Unger describes will tend to obstruct these arteries and may augment occlusive thrombosis formation. There is a significant need for a means and method of minimizing the amount of growth factors for introducing angiogenesis by delivering these agents only to the site where they are most needed.

In addition to a device for delivering growth factors, there are complications with clinically acceptable procedures where special devices for delivering agents to ischemic tissue will be useful. After opening vessels using PTCA, the vessels often lose patency over time. This loss of patency due to restenosis may be reduced by appropriate pharmacological therapy in the region of the artery. There is a need for new techniques that will enable pharmacological therapy to reduce the incidence of restenosis.

Arrhythmogenic Sites

Cardiac arrhythmias are abnormal rhythmic contractions of the myocardial muscle, often introduced by electrical abnormalities, or irregularities in the heart tissue, and not necessarily from ischemic tissue.

In a cardiac ablation procedure, the arrhythmogenic region is isolated or the inappropriate pathway is disrupted by destroying the cells in the regions of interest. Using catheter techniques to gain venous and arterial access to the chambers of the heart, and possibly trans septal techniques, necrotic regions can be generated by destroying the tissue locally. These necrotic regions effectively introduce electrical barriers to problematic conduction pathways.

U.S. Pat. No. 5,385,148 issued to Lesh describes a cardiac imaging and ablation catheter in which a helical needle may be used to deliver fluid ablative agents, such as ethanol, at a depth within the tissue to achieve ablation. Lesh further describes a method of delivering a pharmacological agent to the tissue just before performing the chemical ablation procedure to temporarily alter the conduction of the tissue prior to performing the ablation. Such temporary alteration of tissue has the advantage of allowing the physician to evaluate the results of destructive ablation in that region prior to actually performing the ablation. This method of ablation has the advantage that the ablative fluid agents are delivered to essentially the same tissue as the temporary modifying agents. However, with ablative fluid agents it is difficult to control the amount of tissue which is destroyed—especially in a beating heart, and ablative RF energy is in common use because of its reproducible lesions and ease of control. There is a need for an ablation catheter that provides for both temporary modification of tissue conductivity by delivery of therapeutic agents at a depth within the tissue and delivery of RF energy from the same structure within the heart wall that was used to deliver the therapeutic agents.

U.S. Pat. No. 5,527,344 issued to Arzbaecher describes a pharmacological atrial defibrillator and method for automatically delivering a defibrillating drug into the bloodstream of a patient upon detection of the onset of atrial arrhythmias in order to terminate the atrial arrhythmias, and is herein incorporated by reference. By delivering agents to a blood vessel, Arzbaecher requires systemic effects to be achieved in order to terminate the atrial arrhythmias. The advantages of local drug delivery are completely absent from the system described. There is a need for a system and method to transiently treat atrial arrhythmias by local delivery of pharmacological agents which will effect the excitation of the cardiac tissue locally.

There have been many patents describing systems for delivering anti inflammatory agents to the endocardial surface of the heart. Such surface delivery is less viable for regions at a depth within the tissue. Further, because of the volume of fluid moving by the inner surfaces of the heart, higher concentrations may be required at the surface to counteract the effects of dilution. These higher doses result in greater likelihood of problematic systemic effects from the therapeutic agents. Delivering agents within the tissue will minimize the dilution of agents, and decrease the possibility of the agents being delivered to inappropriate sites. This is particularly important with growth factors whose systemic affects are not well documented, just as it is important for antiarrhythmic agents whose pro-arrhythmia systemic effects have been recognized. There is a need for a means to deliver agents to ischemic and arrhythmogenic sites within the myocardium.

The prior art of devices to deliver substances at a depth within the heart is not extensive. U.S. Pat. Nos. 5,447,533 and 5,531,780 issued to Vachon describe pacing leads having a stylet introduced anti inflammatory drug delivery dart and needle which is advanceable from the distal tip of the electrode. U.S. Pat. No. 5,002,067 issued to Berthelson describes a helical fixation device with a groove to provide a path to introduce anti-inflammatory drug to a depth within the tissue. U.S. Pat. No. 5,324,325 issued to Moaddeb describes a myocardial steroid releasing lead whose tip of the rigid helix has an axial bore which is filled with a therapeutic medication such as a steroid or steroid based drug. None of these patents provide a means for site specific delivery of agents as all applications of the drug delivery systems are at the location selected for pacing. None of these has provided a means or method for delivering agents to ischemic or infarcted tissues. Of these, only Vachon and Moaddeb provide a means for effectively delivering the anti-inflammatory agents to a depth within the myocardium.

U.S. Pat. No. 5,551,427 issued to Altman describes a catheter system capable of delivering drugs to the heart at a depth within the heart tissue.

U.S. Pat. No. 5,431,649 issued to Mulier describes a hollow helical delivery needle to infuse the heart tissue with a conductive fluid prior to ablation to control the lesion size produced. The system does not have drug delivery capabilities.

None of the prior art provides controlled release matrix delivery down a needle or helix to a depth within the heart tissue. None of the prior art provides for a distally located osmotic pump to deliver agents to a depth within the heart tissue. None of the prior art provides a means of delivering agents transiently to a depth within the heart tissue upon demand. None of the prior art provides a means to clear the catheter system of one drug and effectively replace it with a second drug. None of the prior art provides a low impedance conductor to the drug delivery structure for performing ablation after the delivery of a drug. None of the prior art includes the use of macromolecular controlled release matrices such as ethylene vinyl acetate co-polymer to deliver agents with large molecular weights to a depth within the heart tissue.

Local drug delivery provides many advantages. Approaches for local delivery of agents at a depth within a tissue enables the delivery of drugs to sites where they are most needed, reduces the amount of drugs required, increases the therapeutic index of the particular dosing regime, and increases the control over the time course of agent delivery. These, in turn, improve the viability of the drugs, lower the amount (and cost) of agents, reduce systemic effects, reduce the chance of drug-drug interactions, lower the risk to patients, and allow the physician to more precisely control the effects induced. Such local delivery may mimic endogenous modes of release, and address the issues of agent toxicity and short half lives. Approaches for local drug delivery using a catheter based system with a distally located tissue penetrating element have applications in organs such as the heart, pancreas, esophagus, stomach, colon, large intestine, or other tissue structure to be accessed via a controllable catheter.

Local drug delivery to the heart is known. In U.S. Pat. No. 5,551,427, issued to Altman, implantable local drug delivery at a depth within the heart is described. The patent shows an implantable helically coiled injection needle which can be screwed into the heart wall and connected to an implanted drug reservoir outside the heart. This system allows injection of drugs directly into the wall of the heart acutely by injection from the proximal end, or on an ongoing basis by a proximally located implantable subcutaneous port reservoir, or pumping mechanism. The patent also describes implantable structures coated with coating which releases bioactive agents into the myocardium. This drug delivery may be performed by a number of techniques, among them infusion through a fluid pathway, and delivery from controlled release matrices at a depth within the heart. Controlled release matrices are drug polymer composites in which a pharmacological agent is dispersed throughout a pharmacologically inert polymer substrate. Sustained drug release takes place via particle dissolution and slowed diffusion through the pores of the base polymer. Pending application Ser. No. 08/816,850 by Altman and Altman, and Ser. No. 09/131,968 by Altman and Ser. No. 09/177,765 by Altman describe and Ser. No. 09/257,887 by Altman and Altman describe some additional techniques for delivering pharmacological agents locally to the heart. The techniques described herein are all incorporated by reference.

Recently, local delivery to the heart has been reported of therapeutic macromolecular biological agents by Lazarous [94 Circulation, 1074–1082 (1996)], plasmids by Lin [82 Circulation 2217–2221 (1990)], and viral vectors by French [90 Circulation 2414–2424 (November 1994)] and Muhlhauser [3 Gene Therapy 145–153 (1996)]. March [89 Circulation 1929–1933 (May 1994)] describes the potential for microsphere delivery to the vessels of the heart, such as to limit restenosis.

U.S. Pat. No. 4,296,100 issued to Franco describes direct injection of FGF into the heart but specifically does not call out catheter techniques. U.S. Pat. No. 5,693,622 issued to Wolff describes promoters for gene therapy to the heart, but does not enable the delivery of DNA sequences through either vascular or cardiac catheter, or by the injection into the interstitial spaces of the heart.

U.S. Pat. Nos. 5,807,395; 5,431,649 and 5,405,376 issued to Mulier and U.S. Pat. No. 5,385,148 issued to Lesh describe helical needles for use during an ablation procedure, and are limited to ablation catheter uses. They also require the presence of high conductors capable of carrying energy to perform ablation, and do not provide for instruction on how to access different regions of the myocardium and confirm the placement of a device prior to the delivery of fluid agent, nor do they describe a means for guaranteeing that a precise dose is delivered of a particular fluid agent. U.S. Pat. 5,840,059 issued to March describes a means of delivering therapeutic agents into a channel within the heart, but suffers the serious limitation in that the material will likely not be retained in the channels. The viscous carrier suggested by March to help retain the material within the channels poses substantial risk as embolic material should it escape from the channels and be released into the endocardial chamber.

SUMMARY

The devices and methods described below provide for the delivery of small doses of therapeutic agents within the body, in particular the heart. The catheters described below include a distal helical coil or other fixation and penetrating element which can be operated from the proximal end of the catheter to engage and penetrate the myocardium. Once delivered to the inside of the heart, the catheter can be used to inject small doses of therapeutic agents to the myocardium. The drug delivery system of the catheter allows for precise control of the dose injected into the heart wall.

The devices may be used to administer a number of therapeutic agents followed by additional therapeutic agents or passive agents intended to ensure that the intended dose is delivered notwithstanding the dead space of the catheter. Therapeutic agent in the catheter dead space is flushed from the dead space into the heart. Calibrated therapeutic agent reservoirs account for the dead space, and passive agent reservoirs provide a ready source for flushing fluid. The reservoirs may be filled prior to a catheterization, and inserted into a catheter proximal handle so that they are easily operated during the catheterization. The reservoirs are connected to the drug delivery lumen of the infusion catheter through a valve which may be selectively operated to align one or the other reservoir to the drug delivery lumen of the catheter. Additionally, the drug reservoirs may be connected to the valve through flexible distensible lengths of tubing, permitting easy manipulation of the reservoirs for filling and placement in the proximal handle.

The catheter described herein can be used for a number of procedures, including local delivery of angiogenic agents, controlling heart rate during heart procedures and transmyocardial revascularization.

BRIEF DESCRIPTION OF THE DRAWINGS

FIG. 1a shows a partial cross sectional view of a drug delivery catheter.

FIG. 1b shows a cross sectional view of the proximal portion of a dual lumen drug delivery catheter.

FIG. 12 shows an infusion catheter.

FIG. 13 shows a handle of an infusion catheter.

FIG. 15a through FIG. 15f shows a distal end of a steerable guide catheter with a coaxial infusion catheter system.

FIG. 16 shows a steerable guide catheter with a slotted torque tube bending element.

FIGS. 16a, 16b and 16c re cross sections of the steerable guide catheter of FIG. 16.

FIG. 17 shows a distal end of a steerable guide catheter with centrally located infusion catheter.

FIG. 20 shows the distal end of a catheter with pincher fixation means.

FIG. 20a is a cross section of the catheter illustrated in FIG. 20.

FIG. 21 shows a distal end of a helical needle infusion catheter.

DETAILED DESCRIPTION OF THE INVENTION

Figure 1C:
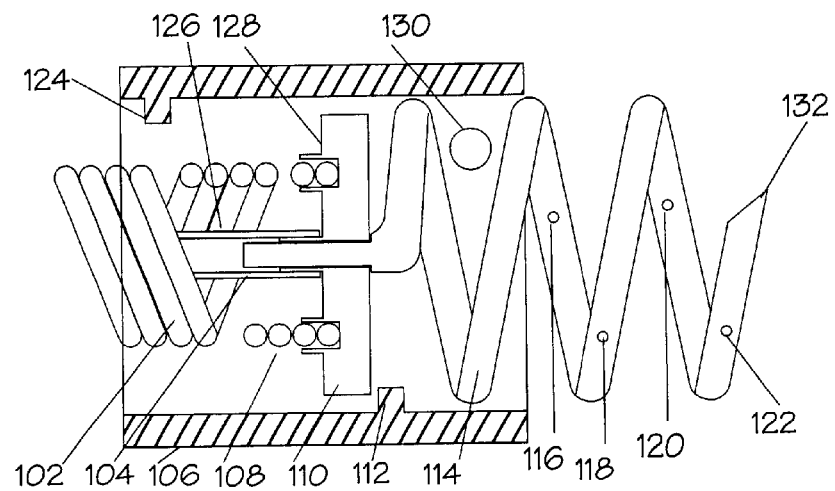
FIG. 1c shows a partial cross sectional view of a distal portion of drug delivery catheter with a hollow fixation helix.

New concepts for delivering agents for the treatment of heart failure, ischemia, arrhythmias, and restenosis are disclosed. The main embodiment consists of transvenous or transarterial catheter delivery techniques for delivering agents directly to a chosen site within the heart at a depth within the heart tissue. Hollow helical delivery devices, needle delivery devices, and implantable controlled release matrices may be inserted such that metabolic agents, anti ischemic agents, growth factors, antiarrhythmic agents, anti-inflammatory agents, gene therapy preparations, and combinations of these agents may be delivered directly to the tissue that can benefit most from these agents. These systems have applicability in many areas of the body, particularly those which may be accessed via a body duct or vessel.

These drug delivery structures may be made from drastically different materials depending upon whether the device is to be used chronically or acutely. For example, metal components in the implantable embodiments which are formed of a Platinum Iridium alloy consisting of ninety percent Platinum and ten percent Iridium will typically be replaced with 316L surgical stainless steels in the acute embodiments. Likewise implantable grades of silicone and polyurethane will be replaced with polyurethanes, polyolefins, fluoropolymers, nylon, and the like in the acute uses of the devices. As a means of addressing this, the term catheter is used to describe both chronically and acutely implantable systems.

FIG. 1a shows a first cardiac drug delivery catheter with a sectional view of the proximal end. Pin 2 is shown mechanically crimped at crimp 6 to electrically conductive helical coil 8. Crimp 6 is typically covered by compliant polymer molding 4 which may form a seal with a catheter port on a drug delivery reservoir or pumping means (not shown). Further molding 4 and catheter body 14 may have external sealing rings to provide fluid tight seals with such ports. Pin 2 connects to internal tubing 10 with lumen 12 which travels the entire length of the catheter to the distal end 22 and allows for fluid agents to be delivered through a fluid pathway in the fixation end 24. The catheter body 14, 20, and 22 covers the coil 8 along the entire length of the delivery system distal to crimp 4 such that rotation of pin 2 or crimp 4 relative to proximal catheter body 14 will result in rotation of coil 8 within catheter body 14, 20, and 22 and deploy fixation mechanisms at fixation end 24. The central lumen 12 in some embodiments may also be used to pass a stylet for use during implantation to facilitate the implantation procedure.

The catheter shown in FIG. 1a differs from those in the prior art in that it is made of permanently implantable materials, it has electrical continuity from end to end for sensing cardiac activity, it has a lumen for conveying fluidic agents along its length, and a hollow fixation means for delivering fluidic agents to a depth within the heart tissue. The materials selected must be able to be implanted for a period on the order of a week without rejection by the patient in order to deliver growth factors over an extended period of time to the patient, or for permanent implantation to provide for transient drug delivery driven by a proximal reservoir and energy source. The catheter body 14, 20, and 22 would be an implant grade polyurethane or silicone, and the distal fixation mechanism at fixation end 24 would be a platinum iridium alloy. The catheter has a single electrode to facilitate implantation by sensing the electrical potential at the implant site. None of the prior art contains this combination which is necessary to achieve the advantages of ease of implantation, and delivery of fluidic agents to a depth within the heart from a proximally located reservoir.

FIG. 1b shows another embodiment of the proximal end of a catheter delivery system in which a second stylet lumen 66 is provided for insertion of a stylet. Such an additional lumen may be useful to prevent contamination of the inner drug delivery tubing 62 during implantation. Inner tubing 62 is connected to pin 52 at connection 56, which may be performed simply by pulling tubing 62 over pin 52 at connection 56. Electrically conductive coil 60 surrounds tubing 62 and may be rotated relative to outer jacket or catheter body 58 of the delivery system. After implantation using a stylet in stylet lumen 66, pharmacological agents may be delivered to the heart by a fluid pathway defined by delivery system lumen 64. The different tubing barriers are shown more clearly in tubing cross section 68. In this specific embodiment, crimp 54 which connects pin 52 and coil 60 is not overmolded, and a single set of seals 70 are shown molded over the proximal end of catheter body 58. Seals 70 prevent migration of fluids into the catheter after connection with a catheter port in a drug delivery reservoir or pumping means. In one embodiment, the distal end of the drug delivery catheter shown in FIG. 1b would be the distal embodiment shown in FIG. 5b. The use of such a second lumen with a drug delivery system for delivery of agents to a depth within the heart does not appear in the prior art.

FIG. 1c shows a partial cross sectional view of a distal portion of a delivery catheter which is to be implanted endocardially by the appropriate venous or arterial access. Here, a simple pathway for fluid to pass from a subcutaneous reservoir or delivery pump (not shown) through a deployable helical needle is provided. Helical coil 102 is shown here as being multifilar, but could be single filar as well. Varying the number of filars allows the flexibility of the catheter as well as the coils ability to transmit torque to the helical fixation structure 114 which is formed of a radio opaque material such as Pt/Ir 90/10. The helical fixation structure is screwed into the heart by turning the coil 102 inside the outer catheter body 106. A fixed structure 130, on the inner wall of the catheter body 106, for advancement and retraction of the helical fixation structure 114, forces the helical fixation structure 114 to advance from the distal end of the catheter when the central helical coil 102 and tube for drug delivery 104 are rotated counterclockwise. Fixed structure 130 is typically formed from a radio opaque material to assist the implanting physician in identifying when helical fixation structure 114 has been deployed. Fixed structure 130 also will retract the helical fixation structure 114 from the heart wall when the coil 102 is rotated clockwise. These directions could easily be reversed by varying the direction of the winding of the helical fixation structure 114. The helical coil 102 which provides torque to implant the helical fixation structure 114 is welded or crimped to the torque delivery structure 110 at the coil to torque delivery structure connection 128. Here, the coil cross section 108 is shown crimped at connection 128. Proximal stop 124, and distal stop 112 are raised portions on the inside of the catheter body 106, and prevent the helical fixation structure 114 from being too far extended or retracted. A fluid path is provided from the proximal end of the catheter (not shown) by tube for drug delivery 104 which connects to the tube fitting 126 of the hollow helical fixation structure 114. The hollow helical fixation structure 114 may have a number of small holes or helix apertures 116, 118, 120, 122 along its length where it is penetrated into the heart tissue. These holes provide a means for delivering agents into the heart tissue at a depth within the tissue. Helix tip 132 is sharp to facilitate penetration of the heart tissue, and acts as a further opening for the agents to migrate from the tissue. In some embodiments the helix apertures may be on only the distal portion of the helix to minimize the possibility of agents being delivered within the heart chambers. In other embodiments, the helix apertures are not present to maximize the structural integrity of the fixation helix. Where this is the case, all agents would be delivered to the heart from the aperture at the hollow helix tip 132. The fixation helix 114 is rigidly attached to the torque delivery structure 110 to provide means for advancement when coil 102 is rotated.

FIG. 1c shows a means for delivering agents by a fluid path to a depth within the heart tissue, and is novel in that it delivers a wide variety of agents by way of a fluid pathway to a depth within the tissue from a proximally located reservoir and is able to transmit electrical energy along helical coil 102 to and from helical fixation structure 114 by way of electrically conductive torque delivery structure 110. It can be viewed as the distal end of the implantable catheter whose proximal end is described in FIG. 10a or FIG. 10b. In one embodiment, the device of FIG. 1 could be used for chronic delivery of antiarrhythmic agents to alter local conduction either continuously, or dynamically on demand based upon the signals sensed through helical fixation means structure 114. Such algorithms have been described for pharmacological atrial defibrillation by Arzbaecher in U.S. Pat. No. 5,527,344. In other embodiments agents for a variety of disease states may be continuously infused by the fluid pathway presented such that they are delivered to a specific site within the myocardium. The proximal end of the catheter may be connected to a drug pumping mechanism or to a proximally located reservoir. Such proximal devices may be implantable or exist outside the patient. Access to implantable proximal devices for refilling agents is easily achieved with a subcutaneous port.

Transient delivery of pharmacological agents based upon demand requires the presence of electrical conductors along the length of the drug delivery catheter to monitor the electrical action of the heart. Delivering of agents upon demand will alter the local conduction or automaticity of the cardiac tissue and allow for the arrhythmia to be treated. A very small amount of drug will be required to treat a specific location within the tissue, which has substantial benefits. A small doses of antiarrhythmic agents will minimize the need to refill the proximally located reservoir; and reduce the systemic effects that result from large drug doses as well as the effects that the agents will have on normally functioning cardiac tissue. In one application of this embodiment, the device would be implanted in the right atrium at a location determined to be most likely to terminate a patients supraventricular arrhythmia. A subcutaneous infusion pump could be triggered by the electrical activity of the heart, and a very small region of tissue would receive local drug delivery for a preprogrammed duration. A small region of heart would then be modified such that cardiac excitation wavefronts would be altered by the tissue treated. This will provide substantial advantages to patients, even if not 100 percent effective. Typical drugs delivered would be antiarrhythmic agents such as those described by in U.S. Pat. No. 5,551,427 issued to Altman.

In a separate embodiment, the device described in FIG. 1c could be an acute catheter made of non-implantable materials. Catheter body 106 would be formed of polyurethane or a fluoropolymer such as ETFE or PTFE; helical fixation structure 114, and torque delivery structure 110 would likely be made of Titanium or 316L stainless steel. Such a catheter would be used for acute ablation procedures in which antiarrhythmic agents are delivered to temporarily alter the conduction of the heart at the site of the implanted helix. Electrical mapping and stimulation measurements may then be made to determine if the region is appropriate to be ablated. If the region is not appropriate the device may be removed and repositioned. If the region affected by the anti arrhythmic agents which effect tissue conduction is desired to be ablated, RF energy may be delivered from the electrically active helix to a large surface electrode, such as that used in electrocautery. The first region ablated will be that equivalent to the surface of the implanted helix. The helical coil 102 is highly conductive to enable RF energy to be conducted to the distal fixation structure to allow ablation of the region immediately at the fixation structure. Such a high conductivity coil could be formed from a number of wires wrapped in parallel in which each wire has a high conductivity silver core jacketed by an MP35N non corrosive alloy. This catheter provides for both temporary modification of tissue conductivity by delivery of therapeutic agents to a depth within the tissue, and delivery of RF energy from the structure within the heart wall that was used to deliver the therapeutic agents. The ablation catheters described in the prior art do not simultaneously provide for drug delivery and ablation from the same structure.

Figure 2:
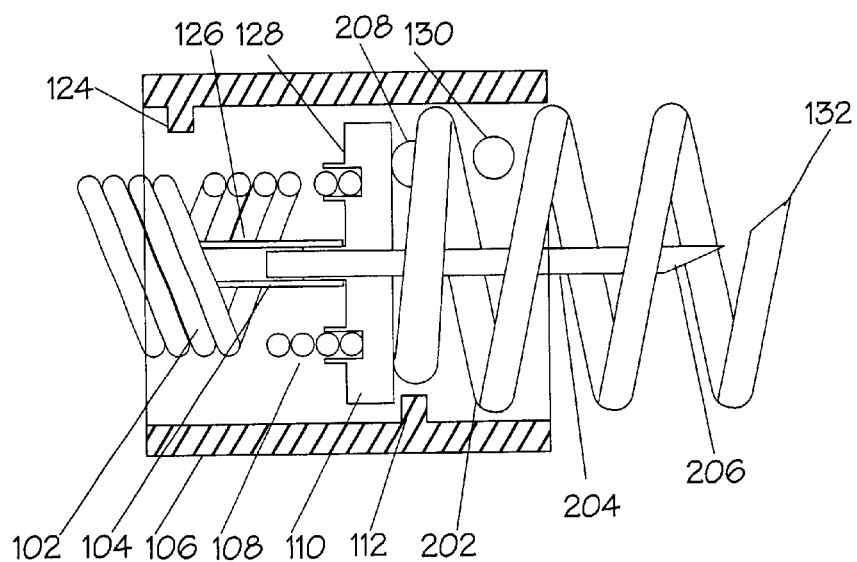
FIG. 2 shows a partial cross sectional view of a distal portion of a drug delivery catheter with a short needle located in the axis of the helical fixation device.

FIG. 2 shows another distal portion of a delivery catheter for endocardial placement. The operation is similar to that shown in FIG. 1, and is applicable to all embodiments described. However, here the solid fixation structure 202 does not provide a fluid path for delivery of agents. The fluid pathway is instead provided by a centrally located hollow needle 204. Apertures could also be made along the needle to provide more exposure to the tissue within the heart wall. Fluid agents may flow down the inside of a connecting tube 104, inside the hollow needle 204, and out through apertures in the surface (not shown) and the needle tip 206. Agents are delivered via the needle to a depth within the tissue. The solid fixation structure advances in the same manner as described in FIG. 1, and may be rigidly attached to the torque delivery structure 110 by a weld 208. Other methods of connection are also possible. The primary advantage of this design is that the solid helical fixation structure 202 is structurally more robust than that of the hollow structure shown in FIG. 1c. This will facilitate implantation of the structure.

Other embodiments which incorporate osmotic pumps, controlled release matrices, membrane barriers, and catheter based transient delivery means increase the ability to control the delivery of agents to a depth within the heart tissue. They have substantial advantages in delivering agents such as growth factors and gene therapy preparations in that very small amounts of the agents are required, the delivery is controlled over time, and the agents are delivered to a depth within the heat.

Figure 3A:
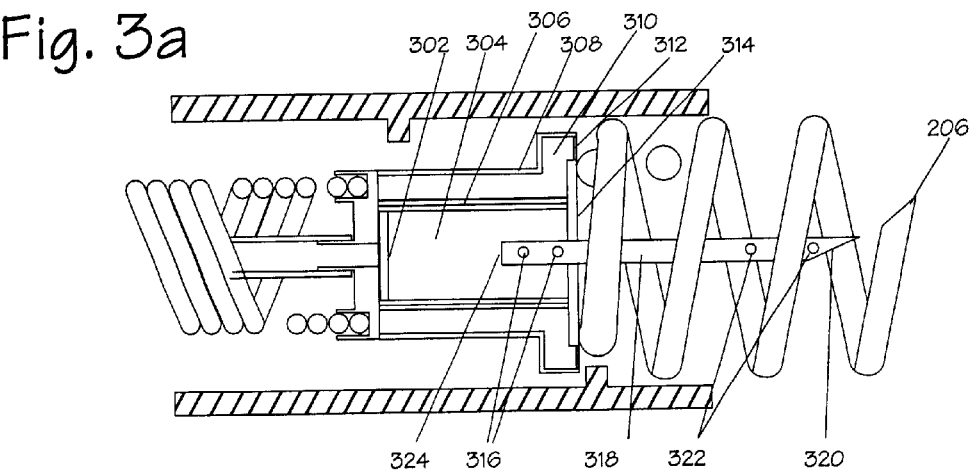
FIG. 3a shows a partial cross sectional view of the distal portion of a drug delivery catheter which incorporates an osmotic pump.

FIG. 3 shows an osmotic pump located at distal end of a catheter to drive therapeutic agent into heart tissue using a needle 318 or hollow helix (not shown) fluid transport system as described. Agents may be delivered via the fluid pathway previously described, through the check valve 302, and into the drug volume or drug reservoir 304. After the drug volume 304 is full, agents will migrate out the needle tip 320, and apertures 322. In this way, the drug volume 304 may be loaded before, during, or after implantation from the proximal end of the drug delivery catheter. Once advanced into the heart tissue, diffusion of water across the semipermeable membrane 312 will occur because of the presence of the osmotic salt 310. As this salt expands with hydration, pressure will be exerted against the flexible barrier 306 and the rigid osmotic pump housing 308. The expansion of the osmotic salt 310 is tantamount to a constriction of the drug volume 304 and as the check valve 302 is closed to reverse flow, the agents are forced through the delivery structure and into the heart wall. Here, the pathway to the needle tip 320 is by way of proximal needle apertures 316 and proximal needle opening 324 within the drug volume 304. The rigid support 314 provides means of supporting the helical fixation means and the needle delivery structure.

Placing an osmotic pump directly at the site where agents are delivered has the benefit of limiting the amount of agent in the system. In devices where the agent in the filling tube can be removed, the site-specific osmotic pump does not require a long length of tubing filled with pharmacological agent. This may be particularly useful for agents whose systemic effects are undesirable or unknown. To deliver agents by a fluid pathway along the length of a catheter system will require a length of tubing to be filled with the appropriate agent. Although minimizing the cross sectional area of such a tube will result in a reduction of the problem of excessive agents, putting the pump at the site for delivery completely eliminates the problem. Placing the osmotic device at the end of the catheter tube provides the advantageous means for follow-up delivery after the pump has delivered all of the agents in the drug volume 304. Further, a very small amount of agent may be all that is required and the osmotic pump may be small enough to be placed on a catheter at the site for delivery. Although catheter based osmotic pumps have been described for steroid elution to the surface of the endocardium, there is no prior art for such catheter based osmotic pumps capable of delivering pharmacological agents at a depth within a tissue with the means disclosed here. Further, there have been no descriptions of catheter based osmotic pumps which may be filled proximally after implant and whose agents may be altered during delivery. Such delivery techniques have substantial advantages for macromolecules such as growth factors and genetic material. Further, they may allow for very controlled delivery of microsphere or micelle encapsulated agents such as may be required for gene therapy.

The drug reservoir can be either a solution or a solid formulation contained in a semipermeable housing with controlled water permeability. The drug is activated to release in solution form at a constant rate through a special delivery orifice. The release of drug molecules or encapsulated drug molecules from this type of controlled release drug delivery system is activated by osmotic pressure and controlled at a rate determined by the water permeability and the effective surface area of the semipermeable housing as well as the osmotic pressure gradient. Devices which use hydrodynamic pressure gradients are similar except the semipermeable membrane is replaced by an opening, and the osmotic salt is replaced by an absorbent and swellable hydrophilic laminate.

Figure 3B:
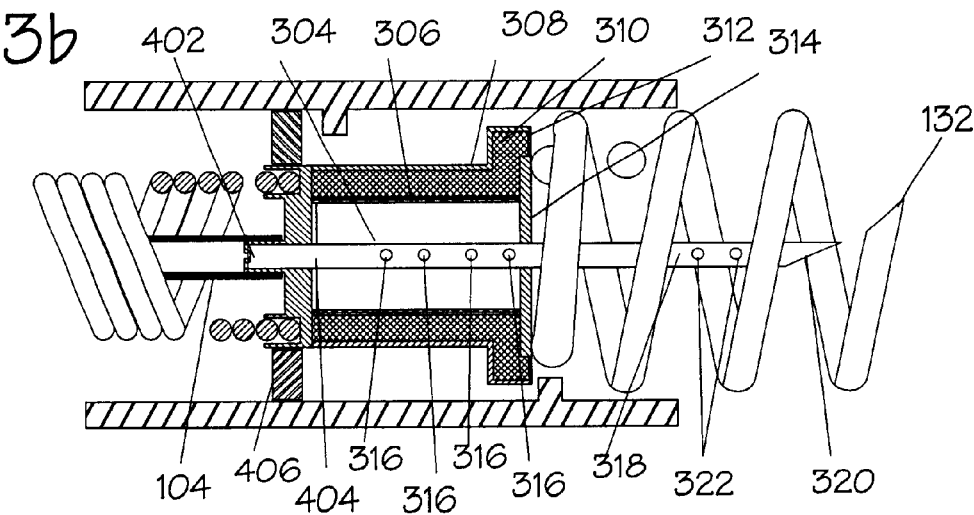
FIG. 3b shows a partial cross sectional view of the distal portion of a drug delivery catheter which incorporates an osmotic pump.

FIG. 3b shows a partially sectional view of another embodiment of the distally located osmotic pump. Here check valve 402 is located at the proximal end of the needle structure 404 which is continuous through the drug volume 304. This needle structure 404 provides more structural stability to the drug delivery device and guarantees that there will be a fluid pathway even after the osmotic action has driven all of the agent out of the drug volume 304. Further, a section of seal 406 is shown attached to the inside of the catheter body. Osmotic pump housing 308 moves within seal 406 which acts to prevent migration of fluids into the catheter body.

Figure 4:
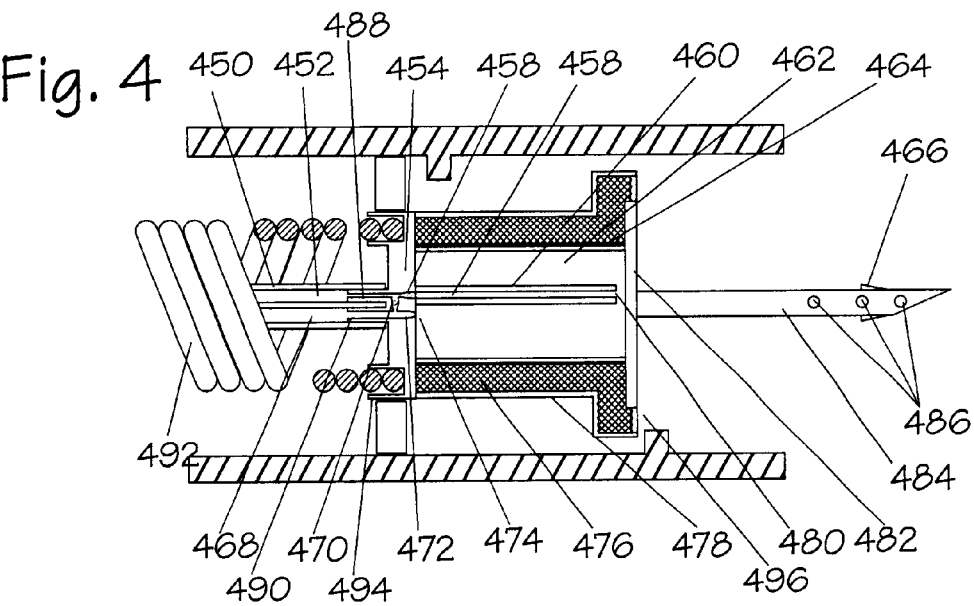
FIG. 4 shows a partial sectional view of a distal portion of a drug delivery catheter.

FIG. 4 shows another embodiment of a cardiac drug delivery system. Here fixation mechanism consists of a needle 484 with apertures 486 that penetrates the myocardium and is held in place by barbs 466. In a chronic implant barb 466 may be composed of either a rigid metallic alloy or a biodegradable polymer. If a biodegradable material is used, long term tissue attachments will maintain fixation with the heart, and the barb 466 will not cause undue trauma should the drug delivery system need to be explanted.

In addition, FIG. 4 shows a multilumen catheter and valve system for the filling of reservoir 462. Agents may be delivered down the fluid path defined by filling lumen 452 in bilumen tubing 450 such that unidirectional check valve 456, shown here as a ball check valve, is opened allowing agents to flow through lumen 458 of tube 460 and out the distal end of tube 480. The ball check valve has a sphere in a generally conical tube which allows unidirectional flow by obstructing the smaller diameter fluid pathway to reverse flow and not obstructing the larger diameter circular pathway of the open flow direction. In various embodiments it could be replaced with a reed check valve, a hinged plate check valve, or the equivalent. After the reservoir is filled, the fluid will open check valve 472 and flow out clearing lumen 468 in bilumen tube 450. This filling action will force ball check valve 470 closed. After filling, the remaining agent in the bilumen tube may be cleared by delivering sterile distilled water, which may contain anticoagulants such as heparin to assure long term patentcy of the catheter lumens, down clearing lumen 468. This clearing fluid will force check valve 472 closed, and check valve 470 open such that agents may be flushed from the bilumen tube and replaced with the distilled water or other flushing agents. If the system is chronically implanted, such a bilumen tube and series of valves would allow one to fill the reservoir 462 and clear the bilumen tube 450 after implant. Further, because the distal end of the tube 480 allows for filling of the reservoir 462 from the distal end, agents may be changed merely by filling via filling lumen 452 which will force the existing agents out through proximal reservoir exit 474, through valve 472 and clearing lumen 468. If the proximal end of such a bilumen delivery system were connected to a dual port subcutaneous reservoir (not shown) agents would be injected into one port while withdrawn from the second port.

In this delivery catheter, the distal housing also acts as an osmotic delivery system with semi permeable membrane 496, hydrophilic salt or agent 476, and flexible polymer barrier 464 allowing for controlled delivery of agents over a period of time. After the expiration of the osmotic energy source, agents may be delivered via the fluid pathway by an external pumping means if desired. The valve housing 454 houses the three unidirectional valves 456, 470, and 472, and provides tube fittings 488 and 490 for connection to the bilumen tubing. This valve housing 454 is also attached by a crimp 494 to the coil 492. This complicated structure would be assembled from the separate components and combined. Separate valves could be fit into openings in a simpler metallic form, and the whole could be mechanically and hermetically attached to the rigid osmotic pump housing 478. Rigid support 482 is rigidly attached to needle 484, and may also have structural elements which enter into the region of the hydrophilic salt, and possibly attach to the valve housing 454. It should be clear that many variations are possible.

Figure 5A:
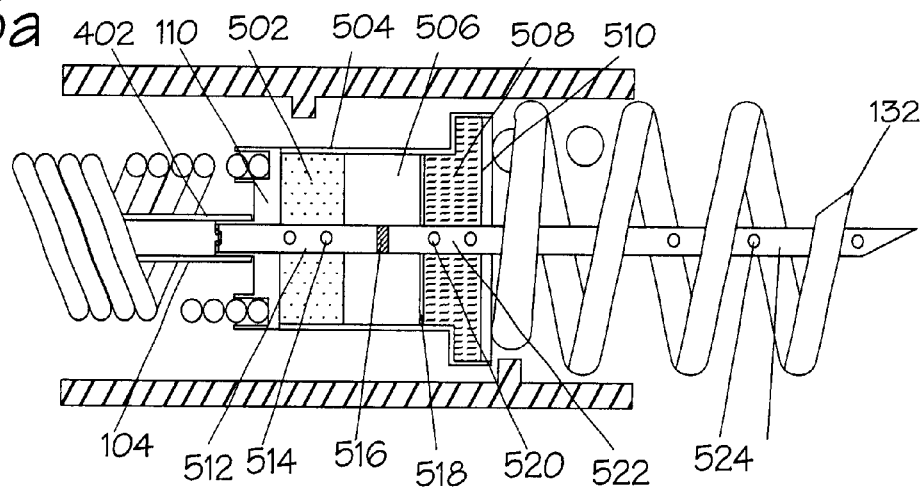
FIG. 5a shows a partially sectional view of the distal portion of a drug delivery catheter with a rate control barrier.

FIG. 5a shows a partially sectional view of an embodiment where a membrane or rate controlling barrier 506 stands between the agent reservoir 502 and the apertures 518 in the proximal end of the delivery needle 520 which would allow the agents to be delivered to the distal end of the delivery needle 524, and through the apertures 522. It is clear that the needle could be replaced with a hollow helical delivery device as shown in FIG. 1c if so desired. Included here is optional controlled release structure 508 for providing chronic delivery of agents to the implant site. As this agent diminishes, new agents can be provided through the connecting tube and check valve 402, such that rate of release is governed by control barrier 506. Barrier 506 is shown here with substantial thickness, but it could be formed of a simple membrane, a membrane reinforced with a substantially porous structure, such as a laminate of expanded polytetrafluoroethylene (ePTFE), or any other structure which could be used to govern the rate of drug delivery to the side of the barrier connected by a fluid pathway to the tissue to be treated. The design of the control release barrier would be customized for the agents to be delivered and may be intentionally designed to specify a rate of delivery substantially different from that which the optional control release structure 508. Needle plug 516 prevents flow through the needle lumen, while maintaining a rigid axial support, and could be formed of an inert polymer or metallic material. Rigid support 510 acts to support axial location of needle 524 and may be a mechanical base for the helical fixation means. Controlled release structure 508 could be composed of a macromolecular controlled release matrix such as EVAC housing a growth factor such as TAF, bFGF, or aFGF.

In another preferred embodiment of FIG. 5A, controlled release structure 508 would be left out and the space would be filled with pharmacological agents and act as a reservoir for acute delivery immediately after implantation. The fluid path for subsequent agents would then pass through tubing 104, through check valve 402, through proximal needle 512 and through proximal apertures 514 into agent reservoir 502, contained by drug reservoir housing 504. The fluid agent must then pass through rate control barrier 506 to be in contact with acute fluid reservoir 508.

In other embodiments of FIG. 5, the control barrier 506 could be electrically activated to allow rapid delivery of positive pressure and agent delivery from one side to the other. In this electrically activated embodiment, the optional control release structure or acute reservoir 508 could merely deliver agents acutely to preserve the viability of the fluid pathway for the time when therapy is deemed necessary. Acute delivery of antithrombolytics and antiinflamitory agents would limit blockages and tissue inflammation resulting from the implantation of the structure in the heart wall and improve the ability of a transient system to deliver agents quickly and effectively to the region within the tissue. An electrically controlled barrier could be fashioned much like any electrically controlled microvalve.

Figure 5B:
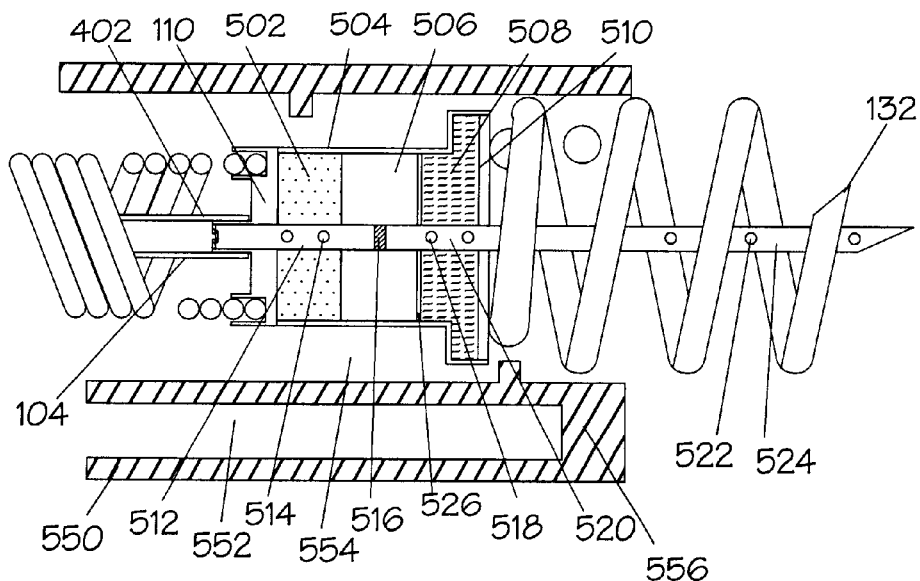
FIG. 5b shows a partially sectioned view of the distal portion of a drug delivery catheter with a second lumen for stylet use during implantation.
Figure 5C:
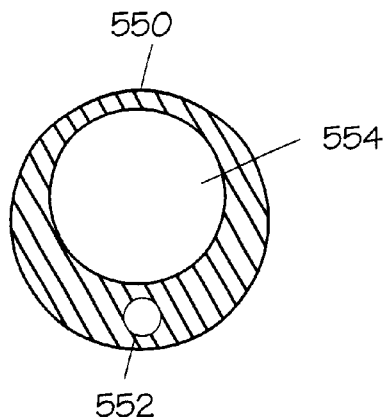
FIG. 5c is a cross sectional view of bi-lumen catheter of FIG. 5b.

FIG. 5b shows a partially sectional view of the drug delivery system described in FIG. 5 which incorporates a separate stylet lumen 552 within the same catheter body 550. Such a stylet lumen will allow for a removable wire element that will allow the implanting physician to control the shape of the device to guide it to the appropriate site. This additional lumen 552 allows the drug delivery tubing to travel the length of the coil in its own lumen 554. Although shown here as a continuous part of catheter body 550, stylet end stop 556 would most likely be attached as a separate component. FIG. 5c is a cross sectional view of bilumen catheter body 550 which shows the diameter of stylet lumen 552 to be substantially smaller than lumen 554. These lumens may change depending upon the requirements for different applications. Such an additional lumen for stylet use could easily be combined with any of the drug delivery systems presented here. This additional lumen will prevent the lumen of the drug delivery tubing 104 shown in these drawings from getting obstructed with body fluids during stylet use, prevent damage to tubing 104 by the stylet, and allow the materials of both stylet and tubing 104 to be chosen without regard to the requirements of the other.

Figure 6:
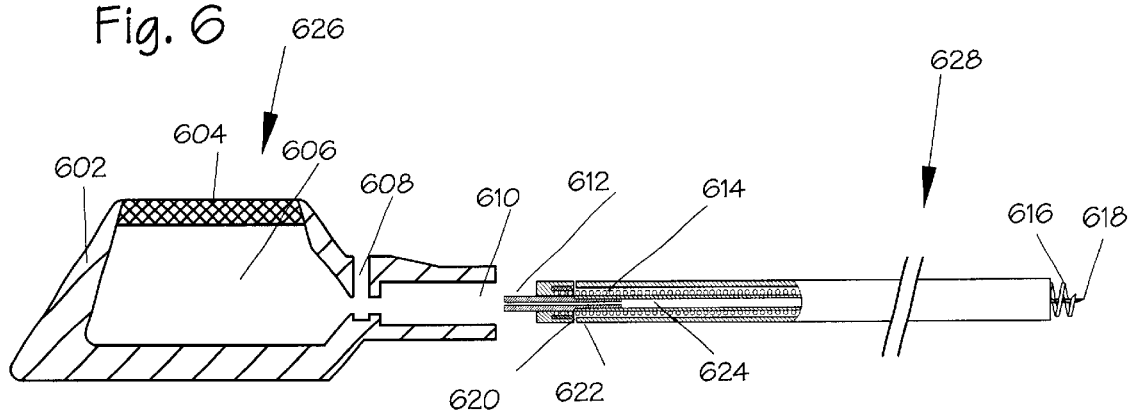
FIG. 6 shows a partially sectional view of a subcutaneous injection port, and a drug delivery catheter.

FIG. 6 shows a partially sectional view of one preferred embodiment of a subcutaneous reservoir 626 and a drug delivery catheter 628 which may be connected to the proximal end of the delivery catheters shown. Subcutaneous reservoir 601 consists of a housing 602 whose reservoir 606 may be filled with a fluid pharmacological agent. The agent is introduced into the subcutaneous reservoir 601 by transcutaneous injection into the reservoir 606 through the polymer injection barrier 604. This barrier is typically composed of silicone rubber such that it creates a seal after removal of the filling needle. In addition, the housing 602 is typically constructed of titanium, polyurethane, or other known rigid biocompatible and non-reactive materials.

FIG. 6 provides a means for connecting the drug delivery catheter to a subcutaneous reservoir, constant pressure pumping means, or transient delivery automatic infusion pumps. Subcutaneous reservoir 626 has a port 610 which accepts the proximal end of delivery catheter 628 such that the region of separation 622 between the crimp structure 620 and proximal end of the jacket body 614 is completely within port 610. This will prevent fluids from entering the separation 622 which allows the coil and inner tubing 624 to rotate relative to the jacket body 614 for advancement of fixation structure 616 and needle delivery system 618. After the proximal end is inserted into port 610 of subcutaneous reservoir 626, a set screw may be advanced within threads 608 to secure the catheter in position by applying force to pin 612. This set screw connection to the pin is common in devices used to deliver electrical therapy to the heart, and could be used to perform an electrical connection to the fixation means 616 or needle 618 in order to sense the electrical activity of the tissue. This electrical signal could be monitored by devices with algorithms similar to those designed to deliver electrical therapy to the heart, accept that instead of electrical therapy they introduce pharmacological therapy.

Figure 7:
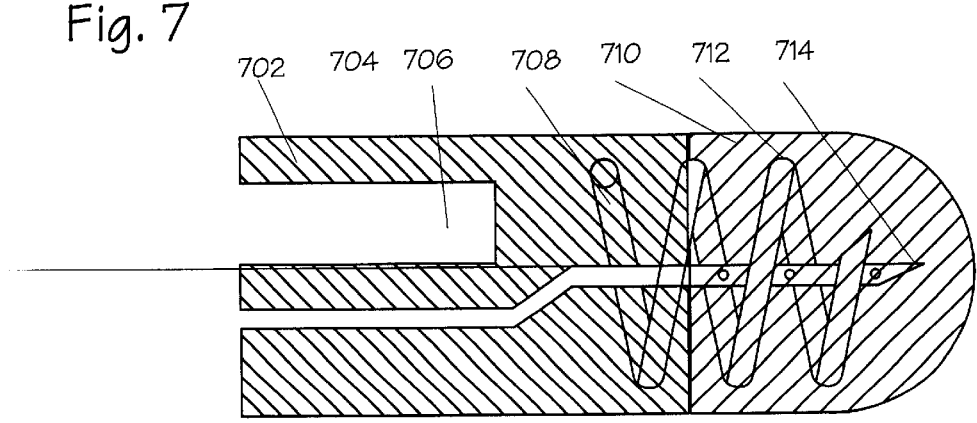
FIG. 7 shows a partially sectional view of the distal end of a drug delivery catheter.

FIG. 7 shows another embodiment of an acute drug delivery system. The catheter body 702 houses a lumen 704 for fluid transport of therapeutic agents and a lumen 706 for stylet use during implantation. Lumen 704 travels the length of the delivery catheter and connects to needle delivery structure 714. During implantation through the vasculature, blood soluble coating 710 completely protects the vasculature from the sharp elements of the helical fixation means 712 and the needle delivery structure 714. Blood soluble coatings such as sugars may be used. After the appropriate heart chamber is accessed, the physician must wait for the coating 710 to dissolve. The coating may be combined with a radio opaque material such as barium sulfate to identify better when this has been accomplished. After the coating 710 has dissolved, the physician implants the helical fixation means 712 by rotating the entire catheter about its own axis. Torque is delivered from the catheter body 702 to the helical fixation means 712 by the embedded portion of the helical fixation means 708. This embedded region can easily be manufactured using molding and bonding technology. The principle advantage of this device is the small cost of manufacturing such a simple design with no moving parts.

Figure 8:
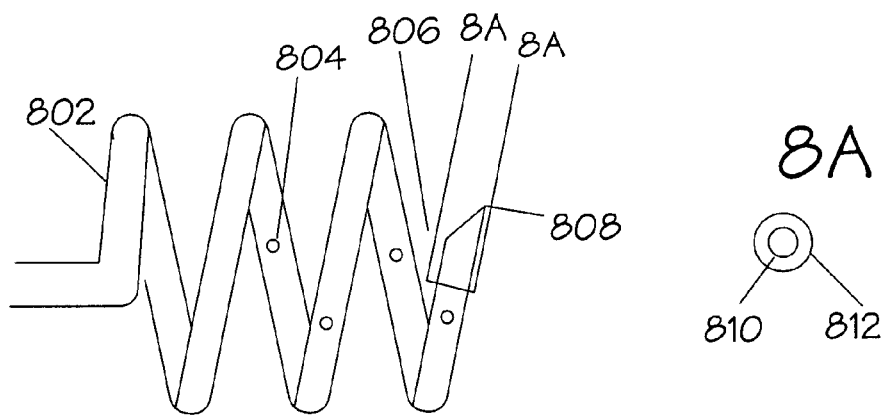
FIG. 8 shows a partially sectional view of a filled helical drug delivery fixation means.

FIG. 8 shows a hollow helical fixation means 802 with apertures 804 along its length. Sectional view of FIG. 8A shows the hollow cross section 812 to be filled with a second material 810. Second material in the preferred embodiment is a controlled release polymer matrix filled with a therapeutic agent for extended delivery of agents through apertures 804 in helical fixation means 802. In one embodiment controlled release matrix is comprised of silicone rubber and the agent to be delivered is lidocaine. In another embodiment the agent may be amiodarone HCL. In another embodiment, the controlled release matrix is EVAC and the agent is aFGF. Other variations are also possible. After implantation of the structure within the heart wall by penetration of helix tip 808, the rest of the helix is rotated such that all apertures 804 are within the tissue. Agents then migrate from the controlled release matrix to the tissue in which it is implanted. Such a controlled release matrix filling of the hollow core which penetrates the heart could be pursued with other penetrating structures as well.

Figure 9:
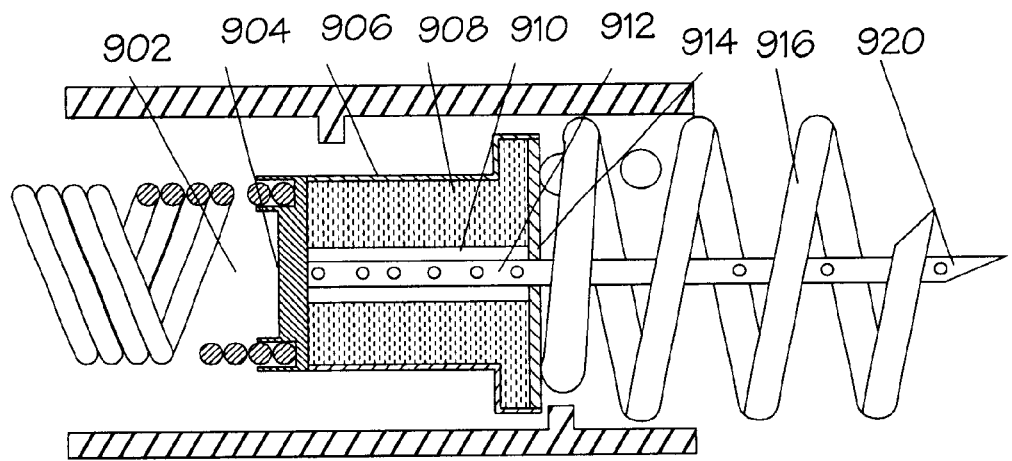
FIG. 9 shows a partially sectioned view of the distal end of a drug delivery catheter.

FIG. 9 shows a drug delivery system with VEGF in an EVAC matrix 908 housed in a reservoir defined by cylinder 906, and ends 904 and 914. In the preferred embodiment, these are non-permeable, although in other embodiments permeability may be desirable. End 904 acts both to transmit torque to helical fixation means 916, but also as a stop for a stylet (not shown) which may be used during implantation down the coil lumen 902. After implantation of the drug delivery catheter, body fluids migrate through apertures in distal needle 920 and into reservoir through proximal needle 912 and dissolve pharmacological agents in acute dosage 910 which may be present to counter inflammation associated with implantation. Over time, growth factors are delivered via needle 920 to a depth within the heart. Note that the absence of a tube for agent delivery enables stylet use during implantation. In variations on this embodiment, other controlled release means could be housed within a semi permeable structure that would allow increased fluid transport to assist in delivery of agents through needle 920 to a depth within the heart wall.

Figure 10A:
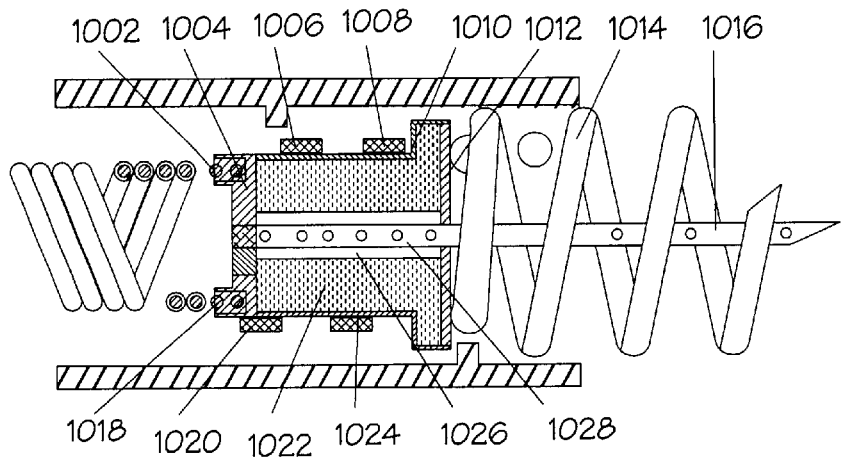
FIG. 10a shows a partially sectioned view of a drug delivery catheter with a nitinol transient delivery means.

FIG. 10a shows another drug delivery catheter in which agents may be delivered transiently to a depth within the tissue. Here, helical coil consists of four co-radial wires 1000a, 1000b, 1000c, and 1000d which are electrically isolated from one another by a layer of insulation. The electrical insulation allows a current pathway to be defined which allows current to flow through electrical connection 1018 of wires 1000c and 1000d and into Nitinol thermally activated shape memory ribbon 1020, which wraps around flexible polymer barrier 1010 and is also shown in cross sections 1006, 1024, and 1008. Current flowing through Nitinol ribbon 1020 completes its circuit to wires 1000a and 1000b at electrical connection 1002 to torque delivery structure 1004 via conduction through connection to support structure 1012 which is electrically connected to needle 1028. Insulating structure 1032 separates the two electrical connection regions on structure torque delivery structure 1004 and allows current to pass through ribbon 1020. If the electrical resistance of the nitinol is relatively high, ohmic heating may prove to be sufficient to cause a constricting shape change upon the flexible polymer barrier 1010. Contained within flexible polymer barrier 1010 is a partially porous polymer controlled release matrix structure 1022 such as silicone rubber containing lidocaine, which upon compression by the nitinol ribbon, will force agents out of the controlled release matrix 1022 and through the needle 1028 within the reservoir 1026 and out the needle 1016 into the heart.

Figure 10B:
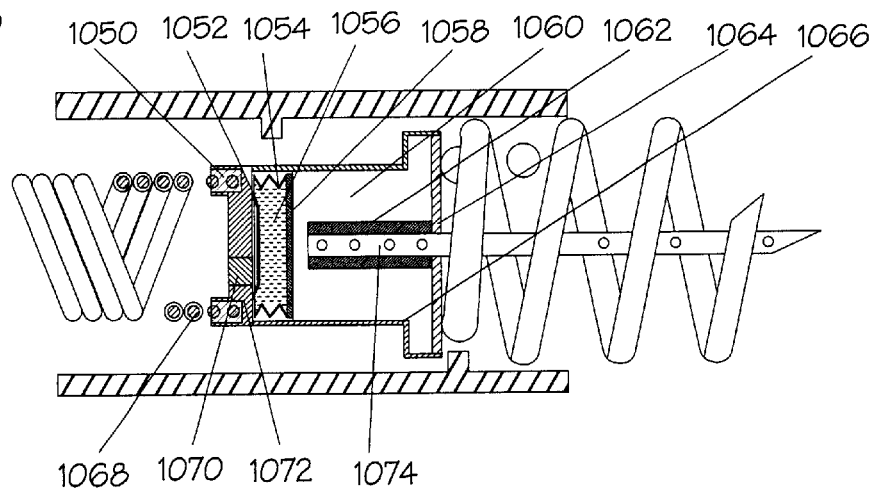
FIG. 10b shows a partial cross sectional view of a distal portion of drug delivery catheter with a vapor pressure transient delivery means.

FIG. 10b shows another transient drug delivery structure in which a reservoir contains a fluid whose vapor pressure provides the energy to deliver therapeutic agents. As in FIG. 10a, the different filars in the helical coil, such as filar cross section 1068, are electrically insulated from one another such that two independent electrical connections may be made at crimp 1050 and crimp 1072 which are separated from each other by electrically insulating barrier 1070. The electrical connections made at crimp 1050 and 1072 have an electrical path between them which is defined by resistive heating element 1052 which passes through reservoir 1056. Within reservoir 1056 is a fluid gas mixture which provides a constant pressure at human body temperature via plate 1058 to the drug matrix 1060. If drug matrix 1060 is a substantially porous controlled release matrix, the pores surrounding the matrix will be filled with relatively high concentration of agents in fluids. As electrical energy is delivered down the two independent electrical conductors to resistive heating element 1052 and increase the temperature of the fluid within reservoir 1056. As reservoir housing 1066 and support structure 1064 are rigid and non-compliant, this will increase the pressure within reservoir 1056, cause expansion of bellows 1054 and apply pressure to the controlled release matrix 1060. This will force the concentrated fluid from within the porous controlled release matrix into proximal end of needle delivery system 1074 and out through the distal needle into the heart wall. Such vapor pressure energy sources have been used in infusion pumps such as Infusaid's infusion pump (Norwood, Mass.). However, it is not known if such a system has ever been implanted on a catheter, or whether the vapor pressure system has provided for a thermal element to increase the temperature within the charging fluid and thus the pressure delivered transiently. In addition to the porous matrix, there is a soluble anti-thrombogenic and anti inflammatory agent for acute in acute dosage form 1062 which surrounds proximal length of needle 1074, while still leaving the end free for agent administration. Such acute dosage forms may be very useful for guaranteeing the long term outcome of such controlled delivery systems by minimizing the response of the tissue to the trauma of implantation.

A method for delivering therapy using a combined drug delivery ablation catheter proceeds as follows. Initially the arrhythmogenic site is located using techniques common to those in the field of cardiac electrophysiology. The delivery system is inserted into the appropriate site within the heart by the internal or external jugulars, cephalic vein, subclavian vein, femoral artery or other vascular delivery routes. Then, the drug delivery structure is implanted at the arrhythmogenic site to supply an appropriate agent for altering the local conduction properties. After implantation, agents are delivered and the effect on the arrhythmogenic site is evaluated by electrical techniques such as mapping. If the location is appropriate, and the agents appear to terminate the critical arrhythmia, RF energy is delivered to the tissue by way of the same structure used to deliver the agents to the heart. If the position is inappropriate and the local pharmacological agents do not correct for the arrhythmia, the device is repositioned, and the procedure is repeated.

A method for transient treatment of supraventricular arrhythmias using a chronically implantable transient drug delivery catheter proceeds as follows. After electrophysiologists have specified the appropriate region for implantation based upon the patient's cardiac electrical action, a catheter is implanted at this site to deliver antiarrhythmic agents at a depth within the heart transiently, as well as to sense the electrical activity near the device. The catheter is then connected to an external controller and power source, which determines suitability of therapy and delivers energy to a device such as those described in FIGS. 10a and 10b for transient delivery of pharmacological agents, or to a device such as that shown in FIG. 1c coupled to a proximally located pumping means. The device then senses cardiac activity through the surface of the drug delivery structure. When the heart experiences an arrhythmic event, the controller identifies the event and activates the energy source which delivers the drug to the heart. This drug modifies the selected area of tissue and either terminates the arrhythmia, or substantially reduces the magnitude of the required electrical therapy. If the arrhythmia does not terminate, the pump may deliver a secondary dosage, or trigger an external electrical therapy device. If no arrhythmia is sensed. The device is maintained in monitoring mode.

Figure 11:
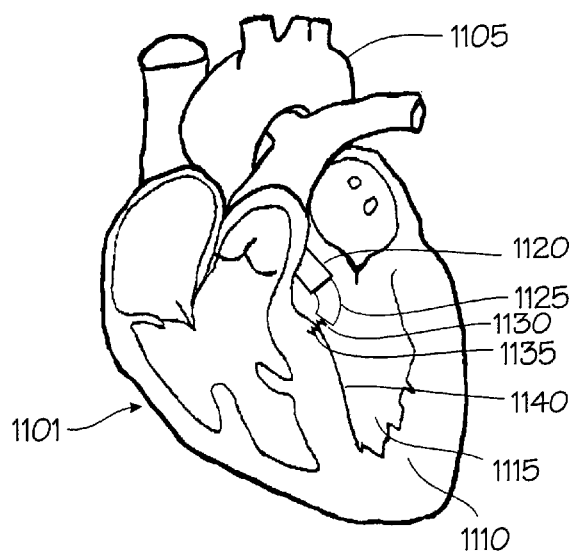
FIG. 11 shows a sectional view of a drug delivery catheter placed through a guide catheter into the left ventricle of a human heart.

FIG. 11 shows a sectional view of the heart 1101 with a triple catheter system passed retrograde across the aorta 1105 and into the left ventricular chamber 1115. Guide catheter 1120 is placed across the tricuspid valve and a steerable guide catheter 1125 is advanced through its lumen in order to target a region of the heart wall 1110 for delivery. Within the steerable guide catheter 1125 is drug delivery catheter 1130. Once oriented towards a region of the heart wall 1110 such as the septal region 1140 shown, the centrally located drug delivery catheter 1130 is advanced into the heart wall 1110 and fixed to the heart tissue by means of the fixation element 1135. In the case of the hollow helical fixation structure 1135 shown, an element in the centrally located drug delivery catheter 1130 must be rotated in order to advance the fixation helix into the heart wall. The catheter system used to implement the inventions described herein can be provided in a variety of configurations permitting delivery and deployment of the fixation tip within the heart. In one alternative embodiment, the outer guide catheter is not used, and only the steerable guide catheter and drug delivery catheter are used. The drug delivery catheter may be a non-steerable catheter within a steerable guide catheter. In a third embodiment, a single steerable drug delivery catheter is used, which also allows for deployment of a distally located penetrating structure such as the helix 1135 shown, with or without a guide catheter. In a fourth embodiment, the single catheter system may be preformed to effect a particular shape within the heart, while allowing deployment of the distally located penetrating structure which is directed to the desired site in the heart by the preformed shape of the preformed distal tip of the drug delivery catheter. In a fifth embodiment, a dual catheter system is used in which the guide catheter is pre-shaped to effect delivery to a certain location, and the drug delivery catheter is delivered from within the pre-shaped system. The preformed shapes are chosen to facilitate preferred orientation of the distal tip of the catheter system in apposition to a desired site of treatment (i.e., the distal opening 1136 is facing treatment site 1137 in the septal wall) when the catheter distal tip is at rest within the heart.

The use of these various systems is similar, but there are subtle differences. For example, in the case where there is an outer guide catheter which is separate from the centrally located drug delivery catheter, the catheter will likely be passed over either a guidewire, or other pre-placed catheter system to gain access to the ventricle. In the case where the system is a single catheter with a deployable infusion element, the catheter can be designed such that the distal curve enables the catheter system to be prolapsed across the aortic valve or steered through and eliminates the need for guiding wires and guiding catheters to access the heart chamber for some physicians. In the cases where concentric catheters are used, there will be concern that blood may enter the very thin space between the catheters, and catheters would be designed with infusion ports to enable the continuous flushing of the space between these catheter systems. Further, these catheter surfaces may be coated with heparin to reduce their thrombogenicity and potential for embolic thrombus formation.

Although ultrasound, radio-opacity, electromagnetic signals, and the like may be used to position the system within the myocardium with techniques described elsewhere, the location of the infusion system once fixed to the tissue is preferentially confirmed visually by flushing the heart chamber with a contrast medium and viewing the radio-opaque penetrating element and catheter body relative to the boundaries of the heart wall. In many cases this will be performed by delivering contrast through a guide catheter, but adjacent separate catheters, as well as distally located contrast lumens within the drug delivery catheter are viable routes for contrast medium to egress into the heart chamber where delivery is desired. Contrast could also be delivered down a drug delivery lumen and into the myocardium to confirm device position, evaluate pharmacokinetics, or visually observe the lymphatic transport away from the region.

The drug delivery catheters with distal fixation devices are beneficially combined with the features described in the following figures, which enable confirmation of position of the catheter and controlled injection of a desired dose of therapeutic agent into the heart wall. The catheter system that has its drug lumen pre-filled with a passive agent such as saline or Ringer's solution to be positioned prior to delivering the therapeutic agents. Once positioned, the therapeutic agent is delivered, and is then followed by a small volume of the passive agent. This subsequent delivery of passive agent will clear the dead space in the catheter, ensuring injection of the entire dose (as measured by the catheter fluid volume) and promote advancement of the therapeutic agent into the myocardium.

FIG. 12 shows a drug delivery catheter with fixed distal penetrating element for implantation within the heart. Catheter handle 1202 is shown with its outer casing removed to illustrate the position of the two syringes 1204 and 1206 within the handle. The syringe plungers 1230 are slidably disposed within the syringes, and are operable from outside the catheter handle with the thumb-slides illustrated in FIG. 13. Prior to delivery of the catheter distal tip 1231 into the heart, the small syringe 1206 is filled with therapeutic agent and large syringe 1204 is filled with passive agent. Syringes 1204 and 1206 are filled in the traditional manner and are then connected attached to distensible tubing 1206 and 1207 with leur fittings 1213 and laid into position within the catheter handle 1202. Prior to insertion of the catheter into the body, the therapeutic agent syringe 1206 is flushed, with stopcock 1210 rotated such that therapeutic agent syringe may flush any air within the syringe into distal drug delivery tubing 1212. Then, also prior to delivery into the body, the stopcock 1210 is turned so that passive agent syringe and its distensible tubing 1208 are aligned in fluid communication with the drug delivery tubing 1212. The drug delivery tubing may be flushed for a full measure of the catheter drug delivery tubing, until the entire tubing length and the distal penetrating element's dead space has been flushed of any air within. The dead space is the volume of the fluid pathway between the reservoir of therapeutic agent and the discharge point at the distal tip of the catheter.

The dead space in many catheters will be equivalent to the amount of drug in a proximally located reservoir that is not effectively delivered to the tissue. This dead volume will cause inaccuracy in dosing, which can be important when small volumes are delivered. It is desirable to have the dead space be small, and the preferred inner diameter of the drug delivery tubing is preferably less than 0.03 cm (0.012"). (In a catheter of 100 cm length, this amounts to a dead space volume of 0.07 milliliters, and in a catheter of 135 cm length, it results in a dead space of about 0.09 milliliters. Preferably, the volume of the dead space is in the range of 0.05 ml and 0.25 ml.) Control of the dead space volume is important to provide good control of the drug dosage into the heart.

One way to eliminate the issue of dead space and dosing errors is to have a post delivery flushing method. Syringe 1204 is larger in diameter than syringe 1206 such that an equivalent displacement of each syringe will result in more fluid being dispersed from the larger syringe. In this way, therapeutic agents may be delivered in volumes less than that of the dead space and followed up by a flushing infusion that will fully clear the remaining therapeutic from the catheter body. This flushing procedure has the advantage that it enables small volumes of agents to be redistributed to some degree by a passive flushing medium such as buffered saline. Additionally, the system may be flushed and filled with the flushing fluid from the second syringe prior to injection of therapeutic agent from the first syringe, so that doses of therapeutic agent which are smaller than the volume of the dead space may be accurately delivered, and expensive therapeutic agent need not be used merely for flushing the system of air bubbles. After the system is initially flushed and filled with the fluid from the second syringe, a predetermined dose of the therapeutic agent may be injected from the first syringe into the dead space of the tube 1212. The injected therapeutic agent is then fully delivered upon being flushed from the dead space by a second injection of the flushing fluid from the second syringe.

The components of the fluids stored in each syringe may be adjusted to provide additional benefits. Dual syringes, coupled to the secure fixation element, provide means to infuse the tissue with one agent, and follow it with delivery of a second potentially synergistic agent without having interaction between these two agents occur before delivery. The second syringe can be loaded with an agent which activates components of the therapeutic agent stored in the first syringe by altering the physical and chemical properties of the first agent. Delivery of the activating agent to exact site is thereby accomplished without manipulation of the catheter system. One example of such a use would be to deliver liposomal preparations from the first syringe, in which liposomes encapsulate a therapeutic compound and protect the therapeutic compound from degrading interaction with the catheter tubing. The liposomes are typically stable within a narrow range of pH, but which are unstable exposed to a different pH. The second syringe can then be loaded with a fluid having a liposome destabilizing pH. When this liposome destabilizing fluid is injected, it serves to clear the dead space of the therapeutic agent and interacts with the liposomes in the first agent to break down the liposomes and release the encapsulated therapeutic compounds simultaneously or shortly after the injection of the therapeutic agent into the heart. In this way, the encapsulated agents are released only after they have been deposited into the tissue and have been flushed with a destabilizing solution which destabilizes and breaks down the liposomes which encapsulate the therapeutic agent. Also, a contrast medium may be used as the flushing medium provided in the second syringe, so that flushing will also serve to mark the location at which the therapeutic agents were delivered. Marking the injection site with contrast agent injected into the wall of the heart facilitates subsequent placement of the infusion needle for additional injections of therapeutic agents.

A luer adapter 1201 for delivering contrast medium is present on the back of the catheter system in this design so that contrast may be delivered through the catheter body tubing 1214 in the space 1230 surrounding the drug delivery tubing 1212. This luer fitting is connected to contrast tubing 1203 which communicates into the Y-adapter 1205 with a suitable bonding or potting agent. The Y-adapter also is bonded to drug delivery tubing 1212 at the proximal end of the drug delivery tubing and to catheter body tubing 1214 at its proximal end. When contrast agent is injected into the leur fitting 1201, it flows through the space between the drug delivery tubing and the catheter body 1214. Small holes may be provided at the distal end of the catheter to enable the contrast to escape, or the penetrating element such as helix 1224 may be fixed over a hollow cylinder 1218 attached to catheter body 1214 by adhesive or other bonding material 1226. Here therapeutic or passive agents are delivered through hollow helical needle 1224 from drug delivery tubing 1212 and contrast is delivered through the annular lumen 1252 between the catheter body 1214 and the drug delivery tubing 1212, then through cylinder 1218. A pressurized source of passive agent, such as saline solution, may be connected to the leur fitting 1201 with a Y-adapter 1251 so that the catheter body may be flushed continuously to prevent the possibility of blood entering between the drug delivery catheter and the catheter body catheters, clotting, and thereafter becoming dislodged into the blood stream. Infusion solutions such as heparinized saline are preferred for this. In one embodiment the inter-catheter space (that is, the annular space or lumen 1215 between tube 1212 and catheter body 1214) could be connected to a gravity fed or pump fed fluid source such that the infusion would be continuous during the procedure. Additional branches could be used such that the catheter could be continually flushed and contrast could be delivered transiently for performing ventriculograms and the like to confirm catheter position.

FIG. 13 shows an enlarged view of the catheter handle shown in FIG. 12 with the cover 1301 in place and the syringe plungers in place on thumb-slides 1306 and 1302. Stops or detents 1312*a*, 1312*b*, and 1312*c* are provided on the outer surface of the cover, in partially obstructing relationship to the thumb slides so that, when the thumb-slides are pushed distally, they encounter noticeable resistance upon meeting any one of the detents, but may be pushed past the detents with additional force applied by the operator of the device. This enables the operator to inject predetermined volumes of fluid (corresponding to the volume of the syringe cleared by movement of the syringe plunger between the detents) by pushing the thumb-slides between detents. These stops may be either visual marks, or they may be physical barriers requiring more force to overcome, or an adjustment to be made before passing. Prior to injection, the stops may be moved along track 1314 such that they can be varied and effect a different dosing regime for a different patient or different agents, if so desired. Slides 1306 and 1302 advance in tracks 1308 and 1304 and engage the plungers, so that the plungers move with the thumbslides, thereby displacing fluid from the syringes and into the drug delivery tubing. (The cover 1301 may be snapped in place after positioning the syringes internally, and may be hinged as shown schematically along line 1318 so that it lifts for syringe placement. A hole 1316 is shown to allow access to the stopcock within, but an alternative structure on the cover 1301 could be placed to engage the stopcock.)

Figure 14:
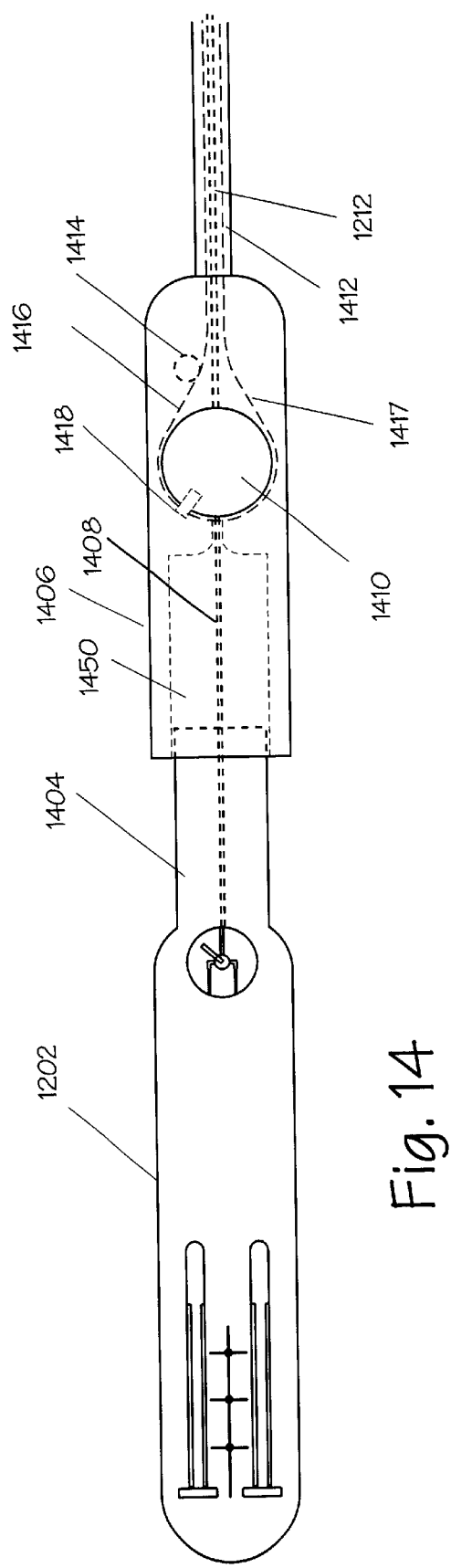
FIG. 14 shows a handle of a steerable guide catheter.

FIG. 14 shows the two piece proximal handling mechanism for drug injection and manipulation of the helical coil attached to drug delivery tube 1212 and steerable guide catheter 1412. FIG. 14 shows the drug delivery catheter handle 1202 and steering handle 1450 in an elevational view. The drug delivery handle has a cylindrical distal end 1404 to facilitate engagement with the cylindrical bore 1451 of catheter handle 1406. The drug delivery catheter may be rotated relative the steering catheter handle, and can be longitudinally advanced and retracted several centimeters while the cylindrical distal end is engaged inside the cylindrical bore. The guide catheter 1412 is steerable, and has at least one pull wire 1416 which is pulled around pulley 1414 and over rotation knob 1410 where it is attached by block 1418. The pull wire is disposed within the side wall of the guide catheter and secured to the guide catheter body at the distal end of the guide catheter, such that rotation of knob 1410 will pull the pull wire 1416 and effect a deflection of the distal tip of guide catheter 1412 (not shown). An additional pullwire 1417 may be provided on the opposite side of the catheter body to provide positive control of the distal tip curvature, rather than relying on the resilience of the catheter tip to effect straightening. In one embodiment, the drug delivery catheter 1408 is placed in the guide catheter prior to steering the guide catheter within the heart in order to prevent the localized bending on the hollow guide structure from causing a kink to form in the distal tip of the hollow catheter. The drug infusion catheter acts to support the guide catheter during the steering process. Such a system may be steered across the aortic valve, or deflected 180 degrees upon itself to prolapse across the valve. The more traditional approach of advancing the steerable guide over a preplaced guide wire, and then following it with the infusion system is also appropriate.

FIG. 15A shows a means for stabilizing the distal portion of the guide catheter to prevent localized buckling. To control steering, it is desirable to have a catheter that will not buckle and which also has a lower bending rigidity in the plane in which the distal structure is to bend. It is also desirable that the distal region of the catheter not be substantially stiff. Braided catheter body 1502 is bonded to the bendable region through standard catheter joining techniques such as an overmolded lap joint. The deflecting region of the guide catheter 1530 comprises a flexible and easily bendable tube 1504 with a coil 1506 disposed coaxially within the tube shown in cross section in FIG. 15*a* 15A and in an elevational view in FIG. 15B. Coil 1506 will prevent the structure from buckling locally. The pullwires 1416 and 1417 are fixed at their distal ends to the distal end of the coil 1506, or to a point in the bending section wall, so that proximal tension on either pullwire bends the bending section. An alternative solution would be to place a number of hoops in the distal portion of the catheter that can move relative to one another. To create the lowest bending rigidity in the desired plane of bending, bending ribbons 1508, 1510, 1520, and 1522 are placed such that their long axes are in the plane perpendicular to the desired plane of bending as defined by the plane in which both pull wires lie. The ribbons may be fixed to the helical coil 1506, or they may rely on adhesives to secure and define their positions within the catheter body. The ribbon and helical coil may also be formed simultaneously by molding them out of higher durometer polymer materials, although they are metallic in their preferred embodiments. FIG. 15B shows that the two pull wires 1416 and 1417 may be attached to the distal portion of these ribbons or even to the distal portion of the helical coil. Again, connecting means are likely to involve crimping, brazing, welding, and combinations of these. Pull wire may also be replaced with a pull cable in embodiments where multiple flexures of the bending element may introduce fatigue. FIG. 15C is a distal end view of the catheter which shows the two ribbons 1508 and 1510 positioned adjacent to the two pull wire lumens 1512 and 1514 (which house pull-wires 1416 and 1417), being disposed within the catheter within the plane established by the two pullwires. FIG. 15D shows a modification of the placement of the bending elements in relation to the pull-wires. The two pull wires 1416 and 1417 are again located in the catheter body wall, defining a plane in which the two pull wires lie, with ribbons 1520 and 1522 being disposed in the plane intersecting the pullwire plane at an angle of about 90 degrees and intersecting the center of the catheter. The preferred bending plane 1530 of the ribbons is parallel with the plane 1531 in which the pullwires lie. FIG. 15E illustrates another embodiment in which four ribbons are placed within the catheter it body wall, distributed at 90 degree intervals around the circumference of the catheter body wall, with the preferred bending planes 1530 of each ribbon parallel to each other, and two pull wires are disposed within the catheter body wall, 180 degrees apart from each other and within the plane 1531. FIG. 15F shows the cross section 15F of FIG. 15A, illustrating the braided catheter body tubing 1502 and showing lumens 1514 and 1512 which enable the pull wires and cables to be pulled by the hand piece with minimal friction.

FIG. 16 shows a steerable guide catheter with two distally located bending segments 1602 and 1604. Bending segments 1604 and 1602 are formed of a slotted hypodermic tube such as that described in U.S. Pat. No. 5,322,064. These two bending elements are formed from the same piece of hypotube with the slots of segment 1602 made at 90 degrees angle from the slots in segment 1604, thereby comprising two sets of slots orthogonally arranged on the circumference of the tube. The hypodermic tubing is covered with thin walled polyolefin material (not shown) and tipped with a soft tip low durometer Pebax or silicone material 1650 at the distal tip. Pull wires are affixed to the tubing by wrapping them around small pins and passing the pull wires through holes in the distal regions of each bending element. Bending segment 1602 has a single wire, shown in the cross section of FIG. 16*a,* disposed within the lumen 1619 in underlying catheter body 1616 with the slotted hypodermic tubing 1618 coaxially overlying the catheter body 1616. The pullwire is anchored at the distal end of the ending segment so that proximal movement of the pull wire causes bending of the segment. The pullwire lumen is oriented at the circumferential center of the cutaway slots, so the bending force is applied along the plane in which the slots have created a bending preference, (that is, the slots are perpendicular to the plane of bending, and establish the preferential bending plane, and the pullwire is located in the preferential bending plane, on the same side of the catheter as the slots. Segment 1604 has an additional pull wire lumen 1621, shown in the cross section of FIG. 16b, the pull wire (not shown) which affixes to the hypodermic tubing near the distal end of segment 1604 and enters through the hypodermic tubing 1618 to enter in lumen 1621 in Pebax tubing 1616. The pullwire 1621 is operable from the proximal end, and translates tension on the pullwire into bending of segment 1614 in the plane perpendicular to the length of the slots. The lumen 1621 is orthogonal, or located 90° from the lumen 1619 relative to the circumference of the tube, so the tip of the catheter can be bent to different degrees in two planes established by the pull wires and the central axis of the catheter. The tubing 1616 runs the length of the catheter and passes within proximal braided catheter shaft 1624, as shown in the cross section of FIG. 16c. Pebax may also be lined with PTFE for lubricity in advancing catheter elements down its length. The catheter shaft 1624 may be formed with a number of sections such that the durometer changes from high durometer to low durometer resin near the distal end of the catheter. The braid can also be varied to affect stiffness and torqueability and in the preferred embodiment is made with 0.0025 inch (0.06 mm) diameter stainless wire with 45 Pics per inch (20 pics per cm). Pull wires connect to proximal pull wire knobs 1614 and 1610 which are disposed one atop another to facilitate ergonomic control of dual axis bending at the distal end. This guide catheter is molded with luer 1612 in place in proximal handle 1612 such that this guide catheter can be used for performing coronary angiograms, left ventricular angiograms, and as a guide for placing other devices and fluid agents within body lumens. In addition to its ability to access the heart, this dual axis steerable guide catheter has many advantages as it may also be slightly modified to enable docking of an infusion catheter handpiece.

FIG. 17 shows a steerable guide catheter similar to the device of FIG. 16 modified by the addition of a docking infusion catheter. Here, infusion catheter handpiece 1710 enters the proximal handle 1714 of the steerable guide which has a narrowing channel 1716 for enabling the advancement of an infusion catheter after the guide has been advanced to its appropriate location within the body over a guidewire. The funnel-shaped narrowing channel 1716 prevents the infusion catheter 1718 from catching and buckling during its advancement into the lumen of the guide catheter. The cylindrical body of the infusion catheter proximal handle 1202 fits into the cylindrical bore of the steering catheter handle. The dual syringe system of this figure is similar to the system of FIG. 12, but has been modified so that each syringe connects to a separate lumen in a dual lumen tube 1750 which traverses the entire catheter length. This bilumen tubing connects directly to the fixation helix 1704, as shown in FIG. 4. Here the dead space for each tubing length remains, but precision of the interaction of the two agents may be controlled at the distal end of the catheter, to achieve the advantages of flushing and interaction already described. In FIG. 17, the distal helix infusion element is shown to be larger than the lumen available within the catheter body, and to taper to a smaller diameter within the catheter body. Such a system cannot be passed from one end of the catheter to the other, but enables the diameter of the catheter to be kept to a minimum. In such a system, the larger fixation structure is essentially garaged in the larger body tubing of the guide catheter tip 1650 or distal bending segment 1602, and can be advanced and rotated by advancing and rotating the cylindrical infusion handpiece 1710 within the guide handpiece 1714. Once advanced just a bit from its garage, space exists between the guide catheter inner lumen and the infusion catheter outer diameter for flushing of contrast agents to improve visualization of the catheter position. Such infusions enable very clear visual confirmation of the engagement of a fixation element with any region desired within the heart when viewed under bi-planar fluoroscopy.

Figure 18:
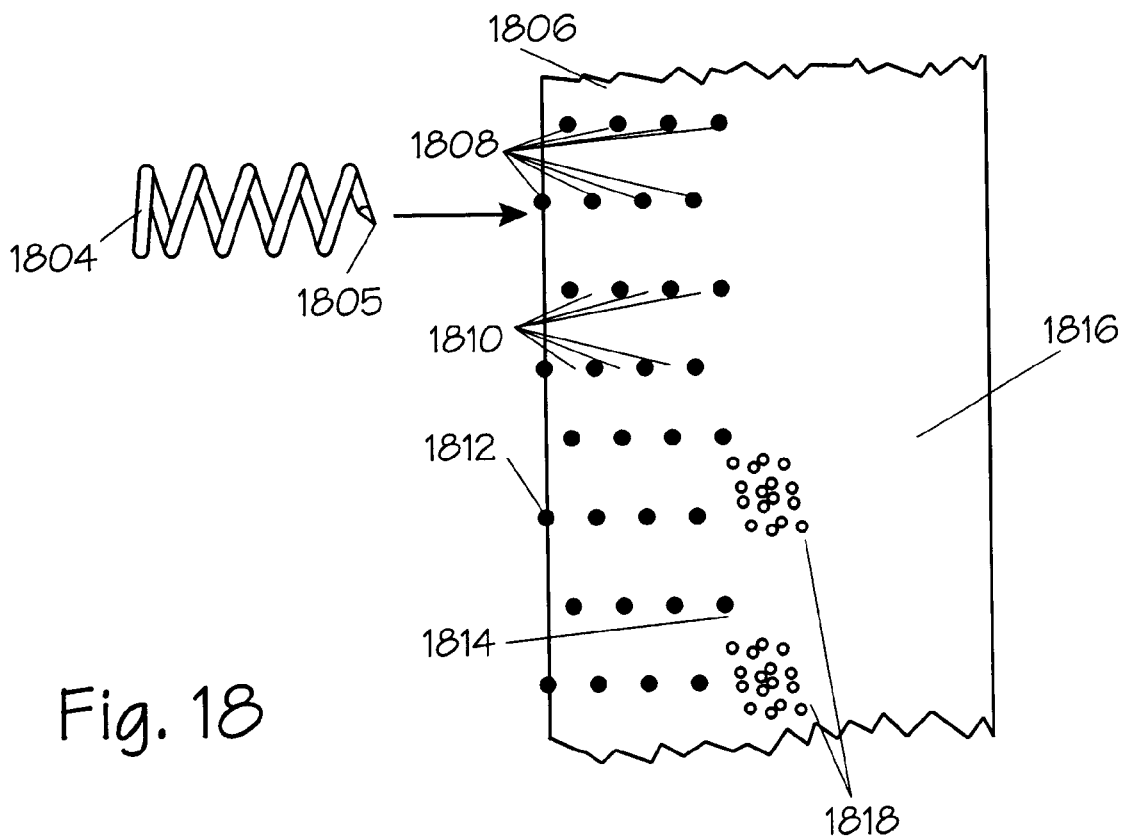
FIG. 18 shows a schematic of a preferred technique for performing percutaneous transmyocardial revascularization and therapeutic delivery with a helical needle catheter system.

FIG. 18 shows a schematic of the helical infusion system being used for percutaneous transmyocardial revascularization (TMR). The helix 1804, which may be delivered to the endocardial spaces of the heart with any of the previously described catheters and methods, is advanced to a depth within the heart tissue, for example the left ventricle wall 1816, is used to create helical pathways of damage within the heart tissue. Cross-section of the helix path in the heart tissue would reveal areas 1808 of damage that corresponds to the needle track. These areas of damage may be beneficial in that these small injuries will trigger endogenous repair mechanisms and reduce angina. Although others are creating straight channels in the heart using lasers, radiofrequency energy, or mechanical coring techniques these systems are less desirable. The helical system shown has the distinct advantage that it maximizes the volume of tissue effected, while minimizing the damage that is introduced (particularly limiting damaged to the endocardium for any given amount of myocardial damage). Simultaneously, damaged tissue 1808 is interleaved with undamaged tissue 1810 through the penetration process. This allows more interaction of healthy tissue with the factors involved in the tissues response to injury. Further, because the helical pathway through the tissue is more quickly self-sealing than the straight puncturing devices currently used, it has large benefits as well. The helical pathway and screw-action required for TMR wounding prevents puncture of the heart and bleeding into the pericardium. The self-sealing helical pathway greatly reduces the risk of life threatening pericardial tamponade being caused by blood entering the pericardium, and also greatly reduces the potential of therapeutic agents 1818 previously or subsequently deposited in the myocardium from leaking into the heart chamber and entering the systemic circulation. Reduced leakage is important to ensure that dosing is appropriately delivered, and critical to prevent the possibility of embolic events occurring when controlled release structures larger than 8 microns in diameter are delivered to the tissue. Agents 1818 in the preferred embodiment are microspheres containing angiogenic agents with a minimum diameter of 30 um in diameter.

A cardiac surgeon performs TMR according to FIG. 18 by inserting the helical needle into a chamber of the heart, for example the left ventricle, and then operating the helical coil to screw it into the heart wall. The surgeon may then inject a small volume of contrast agent through the helical coil into the heart wall to mark the position of the wound. The contrast agent may be incorporated into degradable macromolecules, microspheres or other large molecules described herein to inhibit quick migration within the myocardium and back-leakage from the wound or needle track. The surgeon may then inject a therapeutic agent into the wound, through the helical coil. Again, the therapeutic agent may be incorporated into macromolecules, microspheres or other large molecules to prevent excessively quick migration and back-leakage into the heart chambers. The therapeutic agent may include the patient's own blood, which carries endogenous angiogenic agents. The surgeon may then remove the helical coil by unscrewing it (through operation of the proximal end of the catheter), and perform the penetration on another site within the heart wall. The surgeon will be guided in selection of subsequent sites by the appearance of the contrast agent in the fluoroscopic image of the heart which clearly illustrates areas previously treated.

Typically, the process is repeated to create 4 to 30 wounds in the myocardium.

Figure 19:
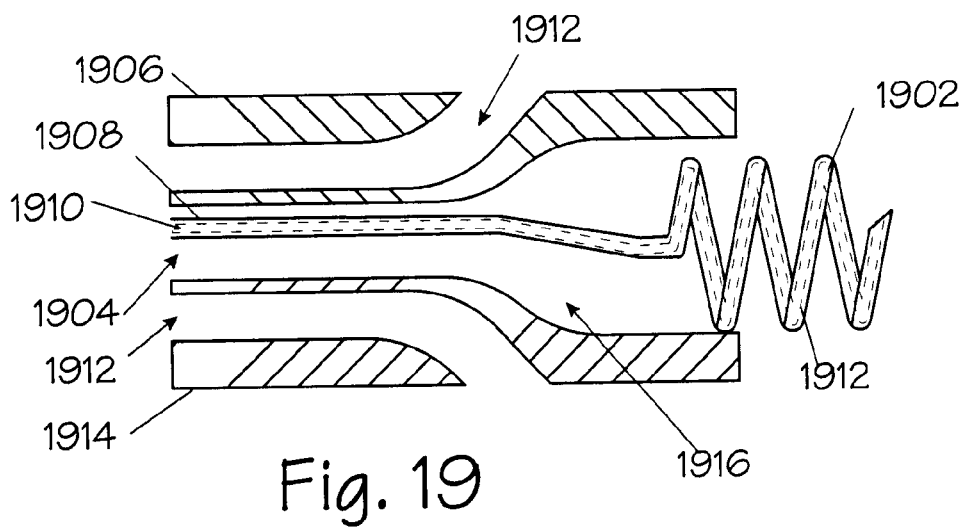
FIG. 19 shows one embodiment of the distal end of an infusion and guide catheter pair.

FIG. 19 shows the distal end of another fixation infusion catheter. The helix 1902 is larger than lumen 1904 in catheter body 1906 and cannot be passed from end to end. However, helix 1902 can be retracted and parked in enlarged distal portion 1916 of lumen 1904 to prevent its being caught on tissue during insertion and manipulation prior to engagement with the heart. Parallel lumen 1912 in the wall of catheter body 1906 provides both a means of infusing contrast adjacent to distally located helix to improve visualization of structures adjacent to the helix as well as the fixation of the helix, and a means of advancing the catheter system over a guide wire. Drug delivery lumen 1910 passes through torqueable pushable catheter body 1908 and connects up to distally located drug infusion helix 1902.

FIG. 20 shows a distal end of an infusion catheter system with pincher fixation element. Here, catheter body 2002 houses pincer fixation lumen 2003, straight needle drug delivery lumen 2012, and utility lumen 2010 which may be used for passing the system over a guidewire (the lumens are visible in the cross section of FIG. 20a), or for infusing contrast near the distal end of the catheter system. The pincer fixation jaws 2006 are opened by pushing on the stylet 2008 and applying tension on the coil element 2004. As the coil 2004 is sized such that it stretches slightly with this force, the jaws will exit the tubing 2002 as they open. Releasing the force on stylet mechanism 2008 allows the jaws to close under a spring action not shown. Once secured to tissue such as the endomyocardium in a fashion similar to a cardiac biopsy, contrast can be infused down utility lumen 2010, to confirm the fixation of the jaws to the endocardium, and a needle can be advanced out of needle lumen 2012. Tubing 2002 may be formed of braiding reinforced Pebax or the equivalent, and the durometer of the tubing resin would be reduced from proximal end to the distal end to optimize the pushability, and torqueability with the flexibility in the heart chamber. For example in a 54 inch length (137 cm) of catheter body tubing, six sections from proximal to distal could be specified: 25 inch (63.5 cm) length of Nylon Vestamid, 1 inch (2.54 cm) section of Pebax 72D, 20 inch (50.8 cm) section of Pebax 63D, 1 inch (2.5 cm) section of Pebax 55D, 1 inch (2.5 cm) section of Pebax 40D, and a 25 inch (63.5 cm) section of Pebax 35D. The entire length would be reinforced with 0.0025", 45 pics Per Inch (20 pics per centimeter) stainless steel braiding.

Similar fixation mechanisms can be envisioned that involve dual intersecting precurved needles, dual needles that are hinged to become trapped in trabeculae, polymer tine structures, and the like.

FIG. 21 shows a distal end of a fixation catheter. Here, the flexibility of the distal end is optimized by incorporating a helical spring with the distal helical infusion element. Approximately six French diameter braided Pebax distal end of infusion catheter body 2102 houses a braided polyamide drive shaft 2104 with an interior diameter of 0.025 inches (0.63 mm) and an outer diameter of 0.045 inches (1.14 mm). Polyamide drive shaft 2104 is connected to helical coil 2106 with an interior diameter of 0.030 inches (0.76 mm) and an outer diameter of 0.039 inch (0.99 mm), the coil being a four filar right hand wound structure with 0.004 inch (0.10 mm) diameter wire. Coil 2106 and polyamide drive shaft 2104 are connected over a Pebax support with an interior diameter of 0.024 inches (0.61 mm) and an outer diameter of 0.030 inches (0.76 mm). A very thin wall 35D Pebax tubing 2105 is melted over the junction of the drive shaft 2104 and the helical coil 2106 and pressure is applied using a appropriately sized heat shrink tubing which is subsequently removed. Drug delivery tubing 2110, shown here to be single lumen tubing having an interior diameter of 0.010 inches (0.25 mm)and an outer diameter of 0.016 inches (0.41 mm) passes within Pebax tubing 2108 and connects to the stainless steel fixation and infusion helix formed of hypodermic tubing having an interior diameter of 0.008 inches (0.20 mm) and an outer diameter of 0.016 inches (0.41 mm) and wound into a helix geometry that has an interior diameter of 0.030 inches (0.97 mm) and an outer diameter of 0.058 inches (1.47 mm). Between the helical coil 2106 and the drug delivery tubing 2110 is a Pebax tube with an interior diameter of 0.016 inches (0.41 mm) and an outer diameter of 0.030 inch (0.76 mm) which adds mechanical support. The use of adhesives, epoxies, and molten polymer resin to adhere these structures together is achieved using standard techniques. In one embodiment, the straight most proximal region of the fixation helix is actually given a slight undulating bend such that it can be embedded in a Pebax material with a mechanical lock to prevent its detachment. This structure altogether provides a means to fix a structure to the heart through a guide catheter and provide substantial flexibility to the distal end.

Figure 22A:
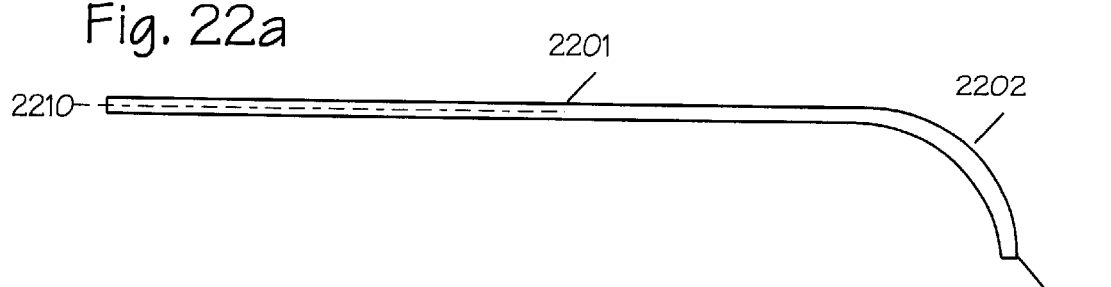
FIG. 22a through FIG. 22c show preformed shapes of guide catheters for accessing different regions in the left ventricle of a heart.
Figure 22B:
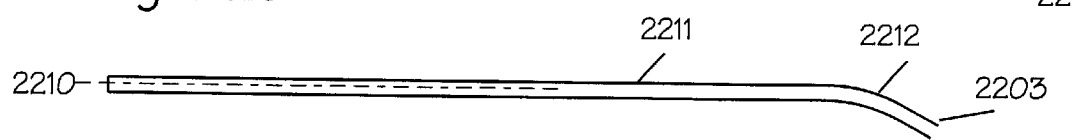
Figure 22C:
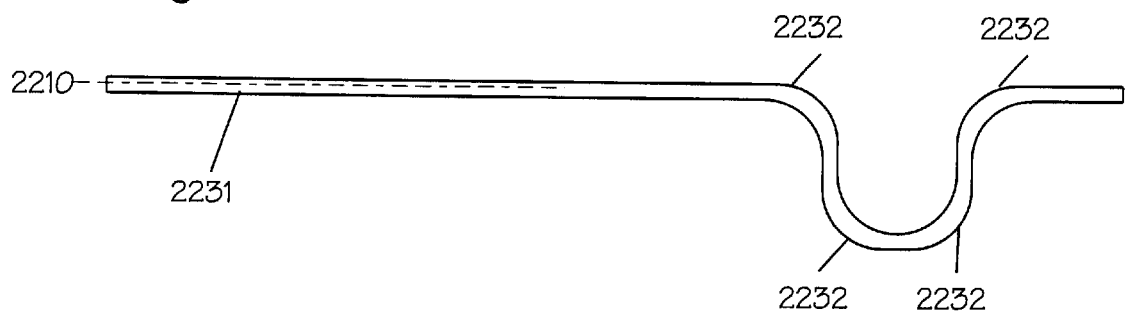

FIG. 22A through FIG. 22C show different preformed guide catheter shapes for accessing different regions of the myocardium. They can be formed in these shapes by placing them over a preformed steel mandrel and placing them in an oven to allow the thermoplastic to reflow. Guide catheters are typically used for accessing the coronary arteries, and these shapes are novel in that they have been designed to access different regions of the left ventricle from a retrograde trans-aortic technique. Guide catheters are typically made of co-extruded or pull-truded stainless steel braiding and PTFE inner layer with an outer liner selected from polyester, blended nylon, Pebax, and the like as has already been described in the description of FIG. 21.

FIG. 22A shows a catheter 2201 with a 90 degree bend 2202 located two centimeters from the distal end 2203 of the guide catheter with the bend radius being around 2 centimeters for accessing the postero-lateral ventricular wall and adjacent regions. FIG. 22D shows a catheter 2211 with a bend 2212 located 1 cm from distal end 2203 of the catheter and deflected off axis (i.e., the long axis of the catheter body when at rest in a straight line) by about 30 degrees for accessing regions adjacent to the inferior left ventricular apex. FIG. 22C shows a catheter 2231 with four bends 2232 each with a radius of curvature of 1.5 cm. They are located 2 cm, 4 cm, 6 cm and 8 cm from distal end of the guide catheter and are all 90 degree bends but in opposite directions as shown. The bend geometry is defined in relation to the long axis of the guide catheter, labeled as item 2210. The distal end of the guide catheter thus is formed with a first 90 degree bend away from the long axis of the catheter at a point about 8 cm from the distal tip, creating a segment of guide catheter running perpendicular to the long axis of the guide catheter, a second 90 degree bend toward the long axis of the guide catheter (bend located 6 cm from the distal tip of the catheter), creating a segment of guide catheter running parallel to the long axis of the catheter, a third 90 degree bend toward the long axis of the guide catheter (bend located 4 cm from the distal tip of the guide catheter), creating a second segment running perpendicular to the long axis of the guide catheter, and a fourth 90 degree bend distally in line with the long axis of the guide catheter (bend located about 2 cm from the distal end of the guide catheter), creating a fourth segment running parallel and co-linearly with the long axis of the catheter, with all bend segments and the proximal segment of the guide catheter lying in the same plane. This catheter is useful for delivering agents adjacent to the anterior wall of the left ventricle as well as the anterior apical regions.

Figure 23:
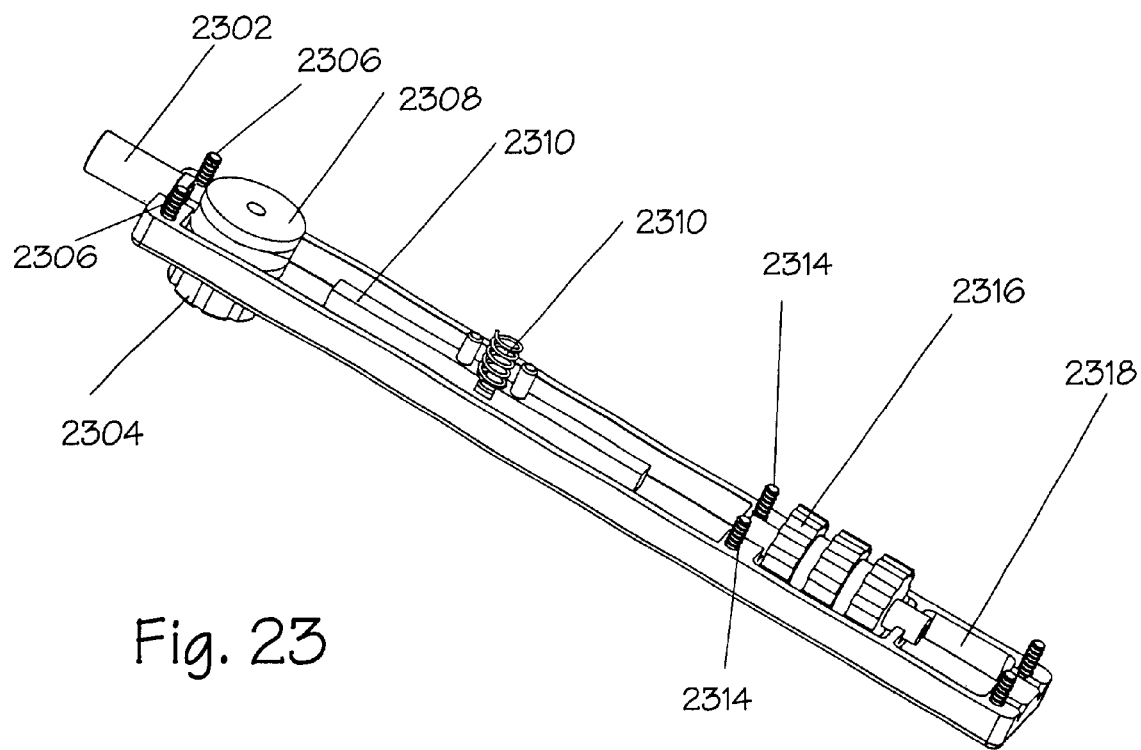
FIG. 23 shows a handpiece for a catheter system.

FIG. 23 shows a handle for a steerable infusion catheter system. The handle is comprised of two matching halves, the lower half 2318 and an upper half that is removed to illustrate the internal components of the handle. One or more steering knobs connect to wheel 2308, which is provided to pull on one or more pull wires in order to effect deflection of the distal end of a steerable catheter. Set screw knob 2304 is attached to wheel 2308 with a screw extension that penetrates the handpiece, so that the position of the wheel (and thus the deflection of the catheter) may be locked into place with set screw knob 2304 which tightens upon the hand-piece 2318. The wheel 2308 is preferably constructed to allow passage of the infusion catheter either through or past the wheel without interference. The wheel may be disposed against the wall of the hand-piece, leaving sufficient space in the center of the hand piece for passage of the infusion catheter, or it may have longitudinal passageway 2350, as shown, which permits passage of the infusion catheter through the wheel (although it may cause slight bend in the portion of the infusion catheter housed within the wheel), in which case the wheel must have a diameter sufficient to cause the desired deflection of the guide catheter with wheel rotation limited by the deflection of the infusion catheter within the wheel passageway. The infusion catheter is slidably disposed in the guide catheter and wheel bypass region, and fixable to the advancement slide 2310. Advancement slide 2310 is slidable within the hand-piece channel, and operable by a thumb slide on the outside of the hand-piece connected to the slide through a slot in the outer surface of the hand-piece. The advancement slide is fixable (though not always fixed) to the infusion catheter so that movement of the slide causes longitudinal movement of the infusion catheter. The travel of the slide is sufficient to allow the distal end of the catheter, including the helical needle, to advance to a desired extent, and may be limited to prevent the possibility that the penetrating element can be extended completely through the myocardium. Once the position of the deflection is fixed by the operator, the infusion catheter is advanced by advancing advancement slide 2310 in channel hand piece channel. (This slide has a spring element 2312 between its two halves to enable the infusion catheter body to pass between fixation clamps in the hand-piece body which is provided in halves (lower half 2318 is shown, and the upper half is not shown in order to illustrate the internal parts of the hand-piece). The two halves of the hand-piece are held together by screws 2306 and 2314. Slide 2310 slides axially within the handle advancing the catheter through a hollow wheel bypass region. Thumb screw 2316 is rotationally fixed to the infusion catheter, so that rotation of the thumb screw causes rotation of the infusion catheter and the helical needle at the distal end of the infusion catheter. The infusion catheter proximal end which lies within the thumb screw region of the hand-piece is longitudinal slidable within the thumbscrews (to permit the sliding controlled by the side 2310), but rotationally fixed to the thumb screw 2316. This may be accomplished by providing the proximal end of the infusion catheter with longitudinally oriented ribs, and providing the internal bore of the thumbscrew 2316 with teeth or cogs which engage the ribs. Once advanced out of the distal end of the catheter, the penetrating helical needle of the infusion catheter is quickly advanced into the heart wall by rotation of thumb drum 2316 which is locked to the catheter body when rotated. Space in the most proximal end of the catheter hand piece is set aside for placement of the coiled tubing and luers that connect to the drug infusion catheter and the outer steerable guide body (not shown). Strain release 2302 prevents damage to the outer guide body. Within the outer catheter body there is also an O-ring seal which is proximal to an outer side port for accessing the outer catheter body lumen. This O-ring is sized to prevent leakage of fluids from the space between the outer guide catheter and the infusing catheter. The location of the O-ring is distal to the longitudinal passageway and proximal to the distal end of the strain relief. Thus, a simple handpiece that provides steerability for the outer catheter body, extension of an inner catheter body with a distal helical infusion element, and rotation of said infusion element is provided.

In use, a surgeon or operator such as an interventional cardiologist inserts the catheter into the body at the femoral artery, using a cut-down or the Seldinger technique to gain access to the artery. The operator then inserts a guidewire into the vasculature and advances a guidewire across the aortic valve into the heart. The operator the inserts the steerable guide catheter system over the guidewire, slides it over the guidewire until the distal tip of the steerable guide catheter is in the heart, and then removes the guidewire. After the guide wire is removed, the infusion catheter system is advanced through the steerable guide catheter, and the patient's own blood is infused through the drug delivery lumen of the infusion catheter system so that albumin will bind to the polymer surface of the catheter lumen (thereby preventing the drugs to be delivered through the lumen from binding to the lumen). Following infusion of blood down the drug delivery lumen, an appropriate medium such as saline or ringers solution is promptly delivered. (Alternatively, saline or ringers containing albumin could be delivered. Likewise, for agents where binding to the polymer walls of the catheter is not an issue, this step would be skipped.) After the lumen of the infusion catheter has been so prepared, the helical infusion needle is screwed into appropriate regions of the heart wall. Contrast is infused through the annular lumen or space between the guide catheter and the infusion catheter to confirm the position of the system under fluoroscopy, and the system is used to inject therapeutic agents, such as microspheres larger than 15 um in diameter, to a depth within the myocardium. The operator forces the plunger of syringe 1206 (FIG. 12) of the therapeutic agent reservoir to force the therapeutic agents into the heart. The amount displaced from the syringe should be equal to the desired dose minus the dead space downstream of valve 1210. Following operation of the therapeutic reservoir syringe, the operator forces passive agent by operation of the plunger of syringe 1204, forcing an amount of passive agent into the drug delivery lumen that is equal to the dead space, to ensure that the entire dead space is cleared of the desired dose of therapeutic agent and that the desired dose is actually delivered to the heart tissue. The catheter is maintained engaged with the heart for a period of time sufficient to ensure that the injected therapeutic agent is absorbed by the heart tissue and does not merely leak out of wound caused by the penetrating helical needle. The catheter is then carefully disengaged from the heart tissue by unscrewing the helix through rotation of the appropriate portion of the proximal handling mechanism. If appropriate, the procedure may be repeated at different locations within the heart.

Fixation infusion systems provide time to confirm the position of the helical needle or other fixation device within the heart during an interventional procedure using electrical signals within the heart tissue, standard fluoroscopic imaging techniques, fluoroscopic techniques in which contrast is infused adjacent to the penetrating element and/or at a depth within the tissue, ultrasound imaging techniques, or even electromagnetic imaging techniques such as those developed by Johnson and Johnson BioSense. Where fluoroscopy is used, contrast agent may be injected through the steerable guide catheter 1624 (FIGS. 16 and 17, or through the annular lumen 1252 of the infusion catheter system. Additionally, contrast agent may be injected into the heart wall through the helical needle after it has been driven into the myocardium, so that the depth of helical needle within the heart wall can be confirmed.

Fixating infusion systems for delivery of therapeutic agents optimizes the control over dosing. Certainty as to the position of the injecting needle eliminates the potential for delivering agents inappropriately, and assures the operator that agents have been delivered to a depth within the tissue. The fixation approach provides the ability to flush the deadspace of the catheter after a procedure to eliminate this potential dosing error, and allows for control over redistribution of the infused agent by controlling the volume and time course of the agent infused. In the case of the helical fixation means, the long path length of the penetrating element (i.e., the needle track) adds the added advantage that agents delivered to a depth within the myocardium will not leak back into the heart chambers, and more dose will reach the target tissue. This has huge advantages in intramyocardial delivery of microsphere controlled release systems which have been sized so that they will not migrate within the myocardium, but which are large enough to cause adverse embolic events should they escape into the left ventricle, but is advantageous also for conservation of all injected therapeutic agents. Typically, when therapeutic agents are injected into the heart wall with a straight needle, much of the therapeutic agent leaks backward, out of the penetration wound (the needle track), and into the endocardial pace (and subsequently into the vascular system to impose systemic pharmacological and thrombotic/embolic effects on the patient). When injecting therapeutic agents with a helical needle, and maintaining the helical needle in place during injection, the rate of back-leakage is diminished. Thus, for a given desired resident dose (the dose remaining in the myocardium after back-leakage of the leaking volume of the therapeutic agent), the necessary injected dose need only be about 2 to 10 times the desired resident dose. Where the therapeutic agent is comprised of macromolecules 10 kilo Daltons and above, and 0.5 cc of therapeutic agent was slowly injected over 30 seconds, followed by injection of 0.2 cc of passive agent injected over 30 seconds, followed by continued retention of the helical needle in the needle track for about 30 seconds, 25% of the dose was retained in the myocardium 1.5 hours after injection. In this case, injection of a dose no larger than about 3–4 times the volume of the desired resident dose is sufficient to provide the desired resident dose.

The fixation means improves physician control of delivering therapeutic agents, genes, and cells for molecular and cellular therapeutic cardiology. The physician can confirm that delivery is appropriate, can infuse agents over any specified time course to a depth within the target tissue, and the physician can deliver other agents at the same sites without fear that the catheter system has moved.

These same systems are useful for a new type of diagnostic procedure in which a fluid agent is infused to a depth within a particular tissue and the fluid is then withdrawn through the same infusion element. In this way a type of fluid biopsy may be performed and the mileau within the tissue may be assessed for the presence of markers of different disease states.

Further the devices described wherein the guide catheter is designed to have a space between it and the fixation systems may be used as a left ventricular angiography catheter with controlled fixation for improved visualization of specific regions of interest within the heart. In use, the endocardial space is accessed as described above, through the vascular system, and the helical needle is driven into the heart wall near the site which is to be visualized in angiography. After the catheter is anchored to the heart wall, angiographic contrast agent is delivered through the guide catheter or through the infusion catheter body (1214 and 1750, for example). The contrast fluid may be injected at high pressure without whipping within the heart and wandering away from the target to be imaged.

Catheters with a straight cylindrical lumen from one end to the other could be used with a thin bundle of optical fibers passed through the lumen to create channels within the heart for improving the flow of pharmacological agents within the heart. In other variations, the thin optical fiber could be replaced with a thin RF electrode structure which could literally burn channels within the tissue. Such procedures could be viewed as a combined transmyocardial revascularization (TMR) and drug delivery. For example, after a catheter is implanted and agents are delivered to minimize re-flow damage to the heart, simple TMR could be introduced with a centrally placed optical fiber. Subsequent to the TMR, angiogenic growth factors could be introduced Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. The method of delivery of a therapeutic agent selected from the set of macromolecule, gene therapy preparation, microspheres, or micelles to a depth within the myocardium including the steps of:

providing a catheter adapted for insertion into the heart, said catheter having a proximal end and a distal end, said catheter having a fixating penetrating element secured to the distal end thereof, said catheter having a drug delivery lumen extending from the proximal end to the distal end of the catheter and a drug delivery port at the distal end of the catheter communicating from the drug delivery lumen to the exterior of the catheter;

inserting the catheter into the heart, and manipulating the fixating penetrating element to engage the heart wall and releasably connect the catheter distal tip to the heart wall;

manipulating the fixating penetrating element to cause it to penetrate the heart wall; and infusing the therapeutic agent to a depth within the heart wall.

2. The method of claim 1 further comprising the steps of:

providing the fixating penetrating element comprising a helical structure; and manipulating the fixating penetrating element to engage the heart wall by screwing the helical structure into the heart wall.

3. The method of claim 1 further comprising the steps of:

providing the fixating penetrating element comprising a plurality of intersecting penetrating elements; and manipulating the intersecting penetrating elements to engage the heart wall by forcing the intersecting penetrating elements into the heart wall.

4. The method of claim 1 further comprising the steps of:
providing the fixating penetrating element comprising a plurality of jaws operable from the proximal end of the catheter to open and close and a penetrating needle longitudinally movable from the catheter into the heart wall; and manipulating the jaws to engage the heart wall and pushing the penetrating needle into the heart wall.

5. The method of claim 1, 2, 3 or 4 in which a confirmatory step occurs after the catheter is attached and before the agent is infused into the tissue, in which contrast agent is infused into the heart chamber to visually confirm that the catheter is positioned appropriately.

6. The method of claim 1, 2, 3 or 4 in which a confirmatory step occurs after the catheter is attached and before the agent is infused into the tissue, in which contrast agent is infused into the heart tissue to visually confirm that the catheter is positioned appropriately.

7. The method of claim 1, 2, 3 or 4 further comprising the step of:

confirming the position of the catheter distal end within the heart by infusing contrast agent into the heart chamber through the catheter.

8. The method of claim 5 in which the contrast is delivered through an outer guide catheter system.

9. The method of claim 7 further comprising the steps of:
providing a guide catheter adapted for percutaneous insertion into the heart, said guide catheter having a proximal end and a distal end and a lumen extending from the proximal end to the distal end;

inserting the guide catheter into the heart;

inserting the catheter through the guide catheter lumen and into the heart;

delivering contrast agent through the guide catheter lumen to the heart.

10. The method of claim 1 in which the contrast is delivered through a distal port in the drug delivery catheter which is fixed to the heart wall.

11. The method of claim 1 further comprising the steps of:
infusing a passive agent in a volume equivalent to 1 to 5 times the volume of the drug delivery lumen.

12. The method of claim 1 in which the volume of the drug delivery lumen in the delivery catheter is between 0.05 and 0.25 milliliters.

13. A catheter for interstitial delivery that has two lumens which connect to one another prior to the distal penetrating element.

14. A drug delivery catheter for injection of small doses of a therapeutic agent into the heart wall, said drug delivery catheter comprising:

a catheter tube adapted for percutaneous insertion into the heart, said catheter having a distal end adapted for insertion in to the heart and a proximal end housed within a housing;

a first lumen extending through the catheter, said lumen having a distal end adapted for fluid injection into the heart and a proximal end adapted for connection to one or more fluid reservoirs;

a first fluid reservoir releasably secured to the housing;

a second fluid reservoir releasably secured to the housing;

a valve communicating with the proximal end of the first lumen, said valve permitting selective connection of the fluid sources to the proximal end of the first lumen;

a first fluid connection connecting the first fluid reservoir to the valve;

a second fluid connection connecting the second fluid reservoir to the valve;

a first actuator for forcing fluid from the first fluid reservoir through the valve and into the first lumen;

a second actuator operably connected to the second fluid reservoir for forcing fluid from the second fluid reservoir through the valve and into the first lumen; and a penetrating needle disposed on the distal tip of the first lumen, said penetrating needle adapted to penetrate the heart wall.

15. The device of claim 14 wherein the first fluid connection comprises a length of distensible tubing.

16. The device of claim 14 further comprising:
a second lumen extending from the housing to the distal end of the catheter, and a third fluid connection in fluid communication with the proximal end of second lumen and adapted for connection to a fluid source, and a fluid port in the catheter at the distal end of the catheter providing a fluid pathway between the second lumen and the exterior of the catheter.

17. A method of injecting therapeutic agents in to the body, said method comprising:

providing a drug delivery catheter for injection small doses of therapeutic agent into the body, said drug delivery catheter comprising:

a catheter tube adapted for percutaneous insertion into the heart, said catheter having a distal end adapted for insertion in to the heart and a proximal end housed within a housing;

a first lumen extending through the catheter, said lumen having a distal end adapted for fluid injection into the heart and a proximal end adapted for connection to one or more fluid reservoirs;

a first fluid reservoir releasably secured within the housing;

a second fluid reservoir releasably secured within the housing;

a valve communicating with the proximal end of the first lumen, said valve permitting selective connection of the fluid sources to the proximal end of the first lumen;

a first fluid connection connecting the first fluid reservoir to the valve;

a second fluid connection connecting the second fluid reservoir to the valve;

a first actuator for forcing fluid from the first fluid reservoir through the valve and into the first lumen;

a second actuator operably connected to the second fluid reservoir for forcing fluid from the second fluid reservoir through the valve and into the first lumen;

placing a first fluid in the first fluid reservoir;

placing a second fluid in the second fluid reservoir;

forcing a predetermined volume of the first fluid from the first fluid reservoir into the first lumen; and forcing a volume of the second fluid from the second fluid reservoir into the first lumen.

18. The method of claim 17 wherein;

the step of forcing a volume of second fluid from the second fluid reservoir into the first lumen precedes the step of forcing a predetermined volume of the first fluid from the first fluid reservoir into the first lumen.

19. The method of claim 17 wherein;

the step of forcing a volume of second fluid from the second fluid reservoir into the first lumen is repeated after the step of forcing a predetermined volume of the first fluid from the first fluid reservoir into the first lumen.

20. The method of claim 17 further comprising:
providing a therapeutic agent in the first fluid;
providing a passive agent in the second fluid.

21. The method of claim 17 further comprising:
providing a therapeutic agent in the first fluid;
providing an activating agent in the second fluid, wherein said activating agent interacts with the first fluid to alter the first fluid.

22. The method of claim 17 further comprising:
providing a therapeutic agent in the first fluid, wherein said therapeutic agent comprises a therapeutic compound encapsulated in a liposome capsule;
providing an activating agent in the second fluid, wherein said activating fluid has a pH which destabilizes the liposome capsules in the first fluid.

23. A drug delivery catheter for injection of small doses of a therapeutic agent into the heart wall, said drug delivery catheter comprising:

a catheter tube adapted for insertion into the heart, said catheter having a distal end adapted for insertion into the heart and a proximal end housed within a housing;

a first lumen extending through the catheter, said lumen having a distal end adapted for fluid injection into the heart through a fixating penetrating element, said fixating penetrating element having a base, and a proximal end connected to a first at least one fluid reservoir; and a second lumen extending through the catheter, said second lumen having a proximal end connected to a second at least one fluid reservoir, and said lumen having a distal end terminating at the base of a fixating penetrating element.

24. A catheter as in claim 23 where the fixating penetrating element is a hollow helix.

* * * * *